United States Patent
Chen et al.

(10) Patent No.: US 10,568,687 B2
(45) Date of Patent: Feb. 25, 2020

(54) INTEGRATED INTRAOPERATIVE DIAGNOSIS AND THERMAL THERAPY SYSTEM

(71) Applicants: The Regents of the University of California, Oakland, CA (US); Med-X institute Shanghai Jiao Tong University, Shanghai (CN)

(72) Inventors: Zhongping Chen, Irvine, CA (US); Gangjun Liu, Irvine, CA (US); Jiawen Li, Irvine, CA (US); Lisa X. Xu, Shanghai (CN); Aili Zhang, Shanghai (CN)

(73) Assignees: The Regents of the University of California, Oaklan, CA (US); Med-X institute Shanghai Jiao Tong University, Shanghai (CN)

( * ) Notice: Subject to any disclaimer, the term of this patent is extended or adjusted under 35 U.S.C. 154(b) by 695 days.

(21) Appl. No.: 14/997,204

(22) Filed: Jan. 15, 2016

(65) Prior Publication Data

US 2016/0206373 A1 Jul. 21, 2016

Related U.S. Application Data

(60) Provisional application No. 62/104,594, filed on Jan. 16, 2015.

(51) Int. Cl.
*A61B 18/14* (2006.01)
*A61B 18/24* (2006.01)
(Continued)

(52) U.S. Cl.
CPC ........ *A61B 18/1492* (2013.01); *A61B 5/0066* (2013.01); *A61B 5/0095* (2013.01);
(Continued)

(58) Field of Classification Search
CPC .......... A61N 1/403; A61N 7/022; A61N 7/02; A61B 18/1492; A61B 18/02; A61B 18/245; A61B 18/1815; A61B 5/0035; A61B 5/0066; A61B 5/0084; A61B 5/0095; A61B 5/4836; A61B 5/0071; A61B 5/6853; A61B 8/12; A61B 8/4416; A61B 8/445; A61B 8/08; A61B 2018/00345; A61B 2018/00386; A61B 2018/00577;
(Continued)

(56) References Cited

U.S. PATENT DOCUMENTS

| 6,517,533 B1 * | 2/2003 | Swaminathan .... A61B 18/0218 600/3 |
| 2001/0007940 A1 * | 7/2001 | Tu ...................... A61B 17/2202 606/41 |

(Continued)

*Primary Examiner* — Lynsey C Eiseman
*Assistant Examiner* — Jessandra F Hough
(74) *Attorney, Agent, or Firm* — Nguyen Tarbet

(57) ABSTRACT

A multimodal medical device for the diagnosis and/or thermal treatment of a disease includes an instrument for performing thermal therapy; and an imaging system having multiple tomographic imaging modes, including optical coherence tomography (OCT), ultrasound imaging, photoacoustic (PA) imaging, fluorescence imaging and/or thermal imaging to provide guidance for accurate diagnosis and treatment of the disease.

5 Claims, 22 Drawing Sheets
(3 of 22 Drawing Sheet(s) Filed in Color)

(51) Int. Cl.
*A61B 5/00* (2006.01)
*A61B 18/18* (2006.01)
*A61B 18/02* (2006.01)
*A61B 18/00* (2006.01)
*A61B 8/08* (2006.01)

(52) U.S. Cl.
CPC .......... *A61B 18/245* (2013.01); *A61B 5/0071* (2013.01); *A61B 8/08* (2013.01); *A61B 18/1815* (2013.01); *A61B 2018/00345* (2013.01); *A61B 2018/00577* (2013.01); *A61B 2018/00982* (2013.01); *A61B 2018/0212* (2013.01); *A61B 2018/1807* (2013.01); *A61B 2018/1861* (2013.01)

(58) Field of Classification Search
CPC .. A61B 2018/00982; A61B 2018/0212; A61B 2018/0231; A61B 2018/1807; A61B 2018/1861; A61B 2090/3735; A61B 2090/378; A61B 2090/3782; A61B 2018/00023; A61B 2018/0022; A61B 2018/00791; A61B 2018/0262
See application file for complete search history.

(56) References Cited

U.S. PATENT DOCUMENTS

| | | | | |
|---|---|---|---|---|
| 2003/0028114 | A1* | 2/2003 | Casscells, III | A61B 5/0077 600/474 |
| 2009/0198309 | A1* | 8/2009 | Gowda | A61B 18/1815 607/102 |
| 2010/0045778 | A1* | 2/2010 | Yelin | A61B 5/0066 348/45 |
| 2011/0137124 | A1* | 6/2011 | Milner | A61B 5/0062 600/160 |
| 2012/0271170 | A1* | 10/2012 | Emelianov | A61B 5/0095 600/439 |
| 2013/0178910 | A1* | 7/2013 | Azamian | A61B 17/00234 607/33 |
| 2016/0022146 | A1* | 1/2016 | Piron | A61B 90/39 600/411 |

* cited by examiner

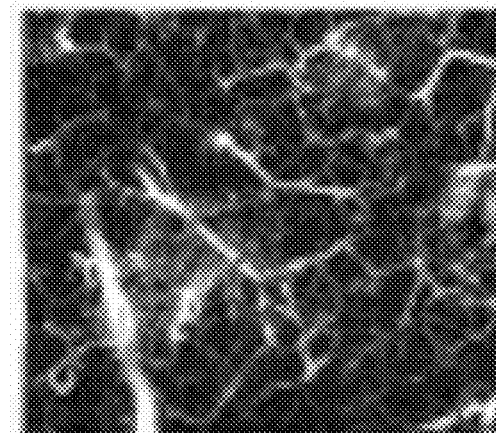
FIG. 23C
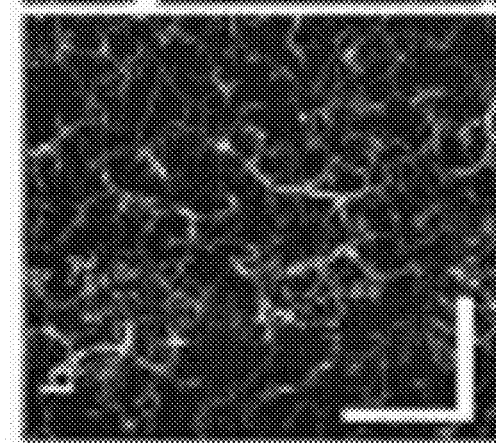
FIG. 23B
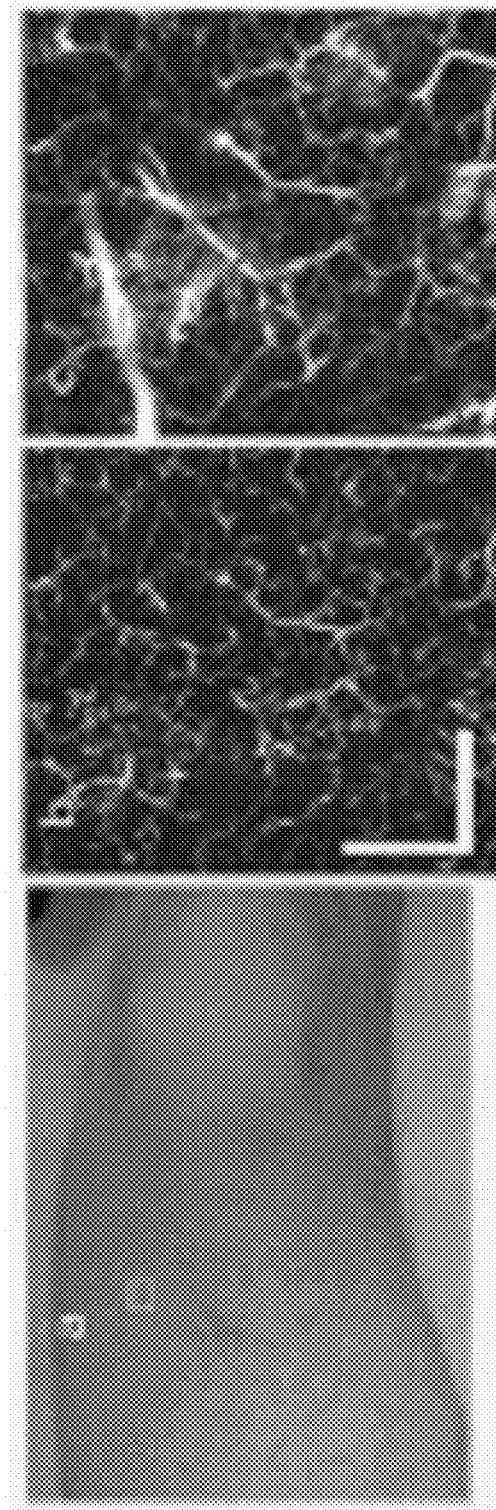
FIG. 23A
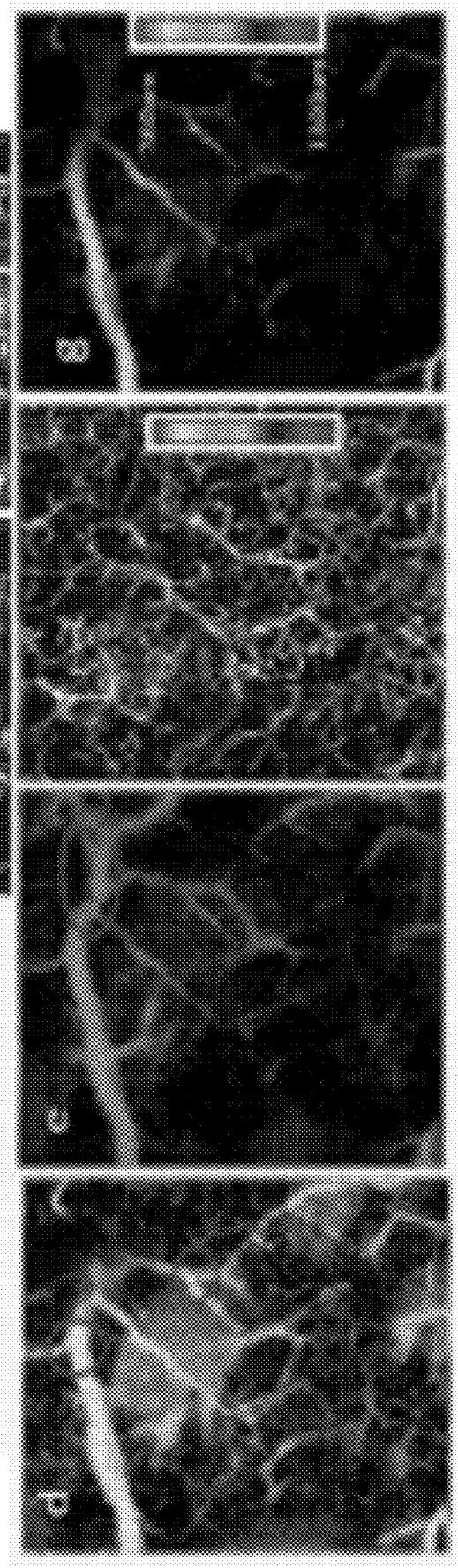
FIG. 23G
FIG. 23F
FIG. 23E
FIG. 23D

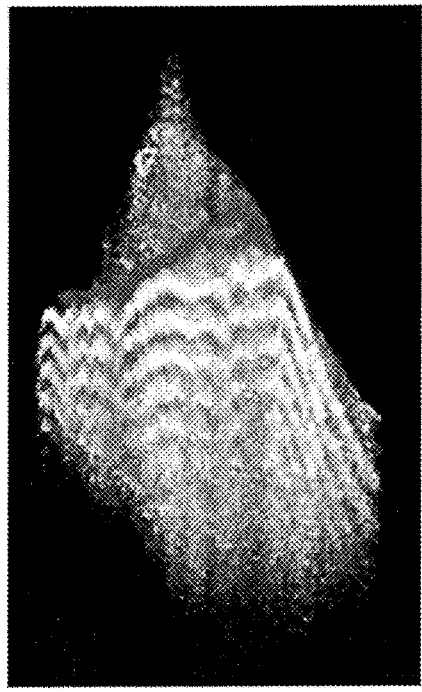
FIG. 26A    FIG. 26B
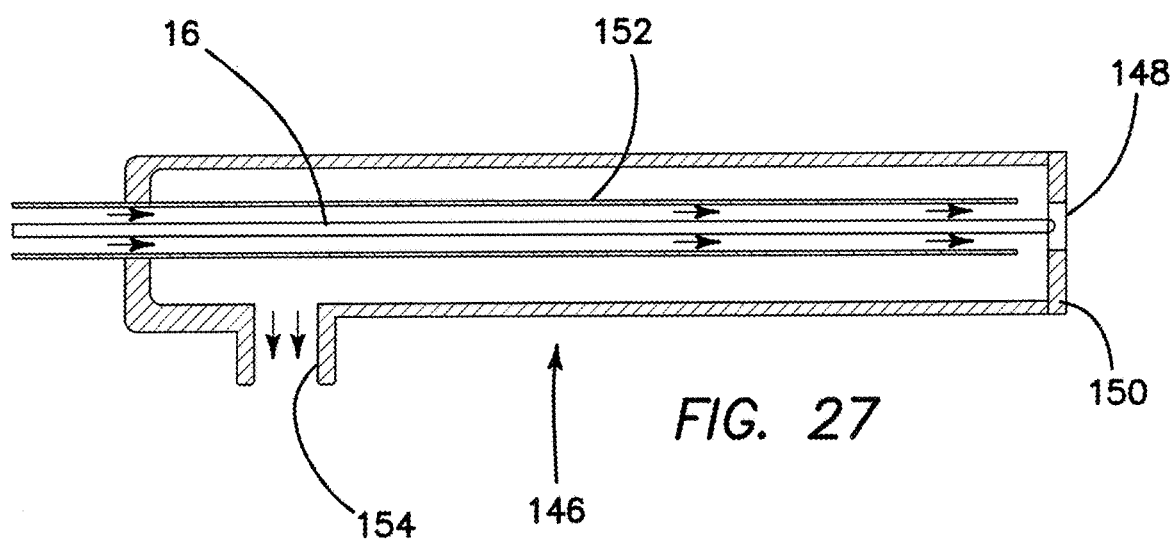
FIG. 27

INTEGRATED INTRAOPERATIVE DIAGNOSIS AND THERMAL THERAPY SYSTEM

GOVERNMENT SUPPORT

This invention was made with Government support under Grant No. EB010090, awarded by the National Institutes of Health. The Government has certain rights in this invention

RELATED APPLICATIONS

This application is related to provisional patent application, entitled, AN INTEGRATED INTRAOPERATIVE DIAGNOSIS AND THERAPY CATHETER SYSTEM Ser. No. 62/104,594, filed on Jan. 16, 2015, under 35 USC 119, which is incorporated herein by reference.

BACKGROUND

1. Field of the Technology

The invention relates to the field of multimodal medical devices and methods for the diagnosis and treatment of cancer, cardiac and cardiovascular disease.

2. Description of the Prior Art

In traditional cardiology and oncology, disease diagnosis and treatment procedures are usually separate. Separate diagnosis and treatment increases the cost and cannot provide timely treatment, which may increase morbidity in some cases. A system which can diagnose and treat diseases simultaneously will greatly decrease the cost and provide timely treatment, which may prevent death from the disease.

Thermal therapy with its relative low cost, few side-effects and short procedure time has been widely used in clinical studies, as an alternative treatment for various diseases besides surgery. Termal therapy here refers to both thermal therapy where tissue is heated to higher temperature and cryotherapy where tissue is cooled to lower temperature. However, without an imaging guidance and a monitoring technique, the accuracy and success rate of a procedure is limited. Consider the problems experienced in the following fields.

1. Cardiology

Coronary artery disease (CAD)/peripheral artery disease (PAD) is the result of the accumulation of plaque within the walls of the coronary arteries that supply oxygen and nutrients to the myocardium. Plaque is made up of fat, cholesterol, calcium, fibrous tissue, and other substances, and over time, the plaque can harden and narrow or block the lumen of the artery. The major cause (86%) of cardiovascular death in heart attacks and the major cause (45%) of deaths from brain aneurysms are from less obtrusive plaques known as "vulnerable plaques" that rupture suddenly and trigger a blood clot or thrombus that blocks blood flow.

For the treatment of CAD/PAD, open surgical revascularization is the standard method of peripheral revascularization because of its high long-term potency rates. However, surgical bypass procedures are associated with periprocedural morbid events, such as wound infection. Endovascular therapy is an alternative to conventional surgical revascularization. However, current endovascular approaches, such as percutaneous transluminal angioplasty (PTA) and stenting, have suboptimal long-term potency. Conventional PTA is limited by high rates of vascular recoil, dissection, and restenosis, especially in the cases of infrainguinal intervention. Although stenting improved periprocedural success by successfully treating vascular recoil and dissection, it still produces unacceptably high restenosis rates and low long-term potency rates, especially for below-the-knee lesions.

Thermal balloon angioplasty (thermoplasty) is a new therapeutic approach for PAD/CAD. It involves the use of cold or heat therapy with angioplasty to treat atherosclerotic plaque, which might improve outcomes and decrease the need for re-intervention. During cryoplasty, the surgeon inserts a balloon catheter into an artery with plaque. Once the balloon catheter reaches the plaque site, the freezing agent is inflated into the balloon. The inflation of the agent due to the higher temperature opens the occluded vessel while freezing the contacted plaques at certain low temperatures. The super-cooling kills local proliferated smooth muscle cells and other unwanted cells while maintaining the vessel structure.

During the heating treatment of the atherosclerosis, high temperature ablates the plaque. Use of the high temperature can easily open up the occluded region in the blood vessel and spare the need of stents. Thermoplasty has been proved to have much better patency rate and lower rate of restenosis.

Besides, according to recent findings, smooth muscle cell abnormal proliferation is involved in both atherosclerosis and restenosis, and these proliferated cells are more sensitive to both low temperature and hyperthermia than the endothelial cells. Thus, through accurately controlled thermal dosage delivery, the endothelium of the blood vessels may also be kept intact during the treatment, which could not been achieved by current treatment modalities and may ensure a much lower restenosis rate after the treatment. Furthermore, the peak temperature rise in vessel wall could be localized in smooth muscle layer while sparing the vascular endothelium through combined RF heating and cooling flow inside a balloon.

Accurate detection of plaque lesions is the first and necessary step in preventing the lethal consequences of atherosclerosis. Traditional angiography only shows an image of the lumen of the vessels; it is impossible for the angiographic image to tell exactly where the atherosclerotic plaque is located. A reliable method for the identification of individuals with atherosclerotic plaques that have a high risk of rupture is fundamental to the selection of patients for vascular intervention. Diagnosis of the latent vulnerability of a plaque lesion relies on tissue structural, chemical compositions, and tissue mechanical properties. The thickness of the fibrous cap, the thickness of the full plaques, the intra-lesion lipid density, tissue mechanical properties are all parameters that correlate with the vulnerability of a lesion.

For over 20 years, intravascular ultrasound (IVUS) imaging has been a standard diagnostic tool for atherosclerosis. IVUS is a catheter-based technique that provides high-resolution, cross-sectional images of the coronary vessel in vivo. In daily clinical practice, IVUS is increasingly used for the visualization of coronary lumen, vessel wall, and atherosclerotic plaque formation. IVUS imaging is performed through cannulation by a catheter with a miniature transducer that emits high-frequency ultrasound, usually in the range of 20 to 50 MHz. As the transducer is moved through the artery, ultrasonic reflections are electronically converted to cross-sectional images. Recent work in IVUS backscatter analysis demonstrated the feasibility and limitation of IVUS to characterize specific lesions and identify plaques that lead to various clinical syndromes. The use of a motorized pull-back device with a defined pull-back speed (0.5 to 1 mm/s) is the established method to image the entire vessel. This permits a volumetric assessment of the vessel and plaque dimensions after longitudinal or 3-dimensional, computer-assisted reconstruction. However, current IVUS has limited resolution and sensitivity to assess the thickness of thin fibrous caps and for plaque classifications.

Recently, optical coherence tomography (OCT) with high resolution, has been applied to intravascular imaging because it enables direct imaging of the thin fibrous cap, circumferential extent of the necrotic cores, and possibly the presence of macrophages in the fibrous cap. All of these are key features of vulnerable atherosclerotic plaque. OCT is a high resolution imaging modality that takes advantage of the short coherence length of broad-band light sources to perform micrometer-scale (μm), cross-sectional imaging of biological tissues. In OCT, imaging contrast originates from sample inhomogeneous scattering properties that are linearly dependent on the sample's refractive indices. OCT offers an axial resolution of 1-15 μm and a penetration depth of around 2-3 mm.

2. Oncology

Thermal therapy has been used for cancer for nearly 50 years. It uses either higher temperature or lower temperature to kill the cancer cells. Compared to other therapies, thermal therapy enables a shorter hospital stay, shorter recovery period, less complications and less pain than with surgery. The induced immunological response by the thermal intrusion offers its great possibility in tumor treatment. However, this high cure rate is not possible in other cancer modalities yet. One reason is the limited high resolution imaging methods for guiding treatment and monitoring treatment at internal body sites to ensure sufficient killing by the thermal treatment, the heating or freezing.

Furthermore, treating tumors with little alteration to the surrounding normal tissue has long been the goal of medical research. In the past two decades, technological advances have brought forth minimally invasive approaches for eliminating undesired tissues. Both cryosurgery and RF heating have attracted a great deal of attention with the help of increased understanding of disease response to freezing/heating and advances in cooling/heating technology. In addition, the use of intra-operative ultrasound guides the placement of cryosurgery probes or the RF/microwave antena. X-ray CT and MRI can also image frozen tissue. However, ultrasound/CT/MRI is limited by its resolution from which it is very difficult to define the fine boundary of the tumor and provide a clear monitoring of tissue deformation under temperature change. OCT gives a ~5 um resolution visualization of tissue, and OCT catheters broaden its applications, such as in bronchial cancer, prostatic cancer, colon cancer and so on.

Lung Cancer:

Radiotherapy and chemotherapy are the standard treatments for lung cancer but have limited effectiveness in reopening obstructed airways. Patients with obstructed airways are not considered suitable for surgery, the other standard treatment for lung cancer, either. Cryosurgery is one of several techniques that can be used to reopen an obstructed tracheobronchial lumen. Cryosurgery is superior than other techniques because of its low cost, few or no side effects and shorter procedure time (~20 mins). High temperature ablation has also been used for lung cancer treatment, the elevated temperature induces both apoptosis and necrosis of the tumor cells and spares the normal tissues by accurate control of the thermal energy.

Pancreatic Cancer:

As estimated by the American Cancer Society, about 45,220 Americans will experience pancreatic cancer in 2013, and 38,180 will die from it. Very few patients survive over five years. Conventional surgery usually kills tumor tissue in pancreas but also crucial blood vessel cells are also destroyed. The pancreas is filled with blood vessels. It is very challenging to kill tumor tissue without heavy bleeding or cuting important nerves by conventional surgery. However, there is one encouraging therapy: cryosurgery. Cryosurgery can kill the tumor cells without damaging the blood vessels. The high temperature ablation has also been proved to be a feasible, safe and promising modality for patients with locally advanced and unresectable pancreatic cancer.

Prostate Cancer:

In North America, prostate cancer is the most common noncutaneous malignancy affecting men and has the highest mortality rate after lung cancer. Even with early intervention and conventional treatment, 30% to 40% of men experience a recurrence of prostate cancer. That means they will need further treatment. Some experts think cryotherapy is an option for treating recurrent prostate cancer. Optical coherence tomography (OCT) has also been adapted for prostate cancer and has been demonstrated to monitore the dynamic process of laser and radiofrequency ablation and identify benign and malignant microscopic structures in the prostate gland ex vivo.

BRIEF SUMMARY

We have invented a multimodal medical device for the diagnosis and treatment of cancer, cardiac and cardiovascular disease. This system combines thermal therapy with several tomographic imaging modes, such as optical coherence tomography (OCT), ultrasound imaging (US), photoacoustic (PA) imaging, fluorescence imaging and thermal imaging guidance to provide accurate diagnosis and treatment of cancer and cardiac and cardiovascular diseases. The current illustrated embodiments of the invention, which can diagnose and treat the disease simultaneously, will greatly decrease cost and provide more timely treatment. Our illustrated embodiments can be applied for the diagnosis and treatment of several kinds of deadly diseases, which include cardiac and cardiovascular diseases and cancer.

This system combines thermal therapy with tomographic imaging and thermal imaging guidance to provide accurate diagnosis and treatment of cancer and cardiac disease. With the help of several low cost imaging modalities, such as OCT, ultrasound imaging, PA imaging, fluorescence imaging and thermal imaging, thermal therapy can be performed with much higher accuracy. Our illustrated embodiments can be applied for the diagnosis and treatment of several kinds of deadly diseases.

The present illustrated embodiments of the invention describe an integrated diagnosis and therapy catheter system (intraoperative imaging catheter) for the accurate diagnosis and treatment of plaques in blood vessels and various types of cancers. An intraoperative imaging catheter can accurately identify the site of lesions and the depth of freezing/heating probe placement, and can monitor the extent of the freezing and/or heating process.

The thermal therapy may use liquid $N_2$ or other agents as the freezing agent for different treatment requirements. Change of freezing agent ensures different freezing treatment capacity. The illustrated embodiments of the invention may use a J-T expansion valve for freezing. The J-T expansion valve is for transportation of the cryoagent into the balloon, one tube for inlet, while the other one as outlet.

The thermal therapy may use radio frequency (RF) for heating. Design of the RF electrodes on the surface of the balloon adjusts the shape and size of the ablation region. RF electrodes can be placed inside the balloon or on the surface of the balloon.

The illustrated embodiments of the invention may use microwaves for heating. The microwave antenna can be placed on the surface of the balloon or inside the balloon.

The illustrated embodiments of the invention may further use infrared light, ultrasound or laser for heating.

The illustrated embodiments of the invention may use fluid or gas at certain temperature inside the balloon to protect the endothelial layer from overheating.

The illustrated embodiments of the invention may further include an infrared (IR) thermal camera for temperature monitoring of treatment. A special fiber bundle may be used for delivering the IR signal through catheter.

The blood vessel which is treated could be any vessel in a patient, including arteries and veins, particularly coronary arteries and peripheral arteries. The cancer type includes but is not limited to lung cancer, liver cancer, pancreatic cancer, prostate cancer and breast cancer.

The illustrated embodiments of the invention may further include intravascular ultrasound imaging (IVUS) into the system so that the cross-sectional images of the vessel wall, entire large lipid pools, and large tumor regions can be visualized. The combination of IVUS and OCT enables us to visualize the vulnerability, location and size of the large plaques/large tumor regions. These parameters are valuable for the guidance of thermal therapy regarding the treatment time, treatment temperature and treatment location.

The illustrated embodiments of the invention may further include PA imaging in the system to provide the mapping of optical absorption distribution of tissue constituents and detection of the chemical composition of tissue. This will facilitate physicians to further validate the region of the plaque and the boundary of the tumor.

The illustrated embodiments of the invention may further include fluorescence cytometry in the system for the diagnosis of cancer.

The illustrated embodiments of the invention may further include fluorescence imaging in the system to accurately image certain molecules in tissue.

The imaging catheter may use a single mode fiber, multimode fiber, dual clad fiber or photonics crystal fiber for the delivery OCT, PA, or fluorescence excitation light and for the collection of OCT and fluorescence signals.

An imaging or several imaging modalities, particularly OCT and/or IVUS and/or PA and/or fluorescence, will be combined and used to accurately identify the location of plaques and tumors. Both OCT-IVUS-PA and a thermoplasty/cryoplasty balloon or thermal probe may be integrated into a single catheter so that the whole operation time is greatly reduced and patient safety is enhanced. In addition, the inclusion of OCT IVUS-PA during thermal therapy greatly increases diagnosis accuracy since the OCT-IVUS-PA can also be used to monitor the thermal therapy process in real time to improve the treatment effectiveness and accuracy.

The illustrated embodiments of the invention may further use functional extensions of OCT, such as Doppler OCT (including phase resolved Doppler, Doppler variance, intensity based Doppler and Doppler variance, Doppler angiography, etc.), polarization sensitive OCT for the imaging of vasculature, collagen, cartilage and nerve. The word OCT technology in this document includes functional extensions of OCT technology.

The illustrated embodiments of the invention may include a Doppler OCT function and polarization sensitive OCT function to provide assessment of treatment boundary and tissue damage.

The OCT imaging probe may be configured to have a side view design or forward view design and may be rotated by an external motor or a distal-end micro motor. A forward view OCT probe may use a lead zirconate titanate or PZT material, or more generally a piezoelectric material or electromagnetic (EM) design. The OCT probe may use a gradient index (GRIN) lens or GRIN fiber or a ball lens in combination for the purpose of focusing.

The illustrated embodiments of the invention further improve the treatment by incorporating dual or multiple balloons with the catheter. One balloon will be used for cryoplasty and/or thermal therapy and another balloon will be used for isolation. Under the guidance of the OCT image, the location of the plaque will be accurately diagnosed and located. Typical plaque only exits on one side of the vessel. With this arrangement, only the side with plaque will accept the cryoplasty therapy and the other side will not be affected by the cryoplasty therapy. This will increase the treatment accuracy and minimize unnecessary treatment of healthy tissue.

While the apparatus and method has or will be described for the sake of grammatical fluidity with functional explanations, it is to be expressly understood that the claims, unless expressly formulated under 35 USC 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 USC 112 are to be accorded full statutory equivalents under 35 USC 112. The disclosure can be better visualized by turning now to the following drawings wherein like elements are referenced by like numerals.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 4b is a schematic side cross sectional view of an alternative embodiment of the fiber rotatory joint (FRJ) based sized view rotational imaging catheter probe seen FIG. 4a.

FIG. 4c is a schematic side cross sectional view of an alternative embodiment of the fiber rotatory joint (FRJ) based sized view rotational imaging catheter probe seen FIG. 4a.

FIG. 4d is a schematic side cross sectional view of an alternative embodiment of the fiber rotatory joint (FRJ) based sized view rotational imaging catheter probe seen FIG. 4a.

FIG. 5b is a schematic side view of an alternative embodiment of the MEMS-motor based sized view rotational imaging probe seen in FIG. 5a.

FIG. 5c is a schematic side view of an alternative embodiment of the MEMS-motor based sized view rotational imaging probe seen in FIG. 5a.

FIG. 5d is a schematic side view of an alternative embodiment of the MEMS-motor based sized view rotational imaging probe seen in FIG. 5a.

FIG. 6b is a schematic side view of an alternative embodiment of a fiber actuator based front view imaging probe seen in FIG. 6a.

FIG. 6c is a schematic side view of an alternative embodiment of a fiber actuator based front view imaging probe seen in FIG. 6a.

FIG. 6d is a schematic side view of an alternative embodiment of a fiber actuator based front view imaging probe seen in FIG. 6a.

FIG. 6e is a schematic side view of an alternative embodiment of a fiber actuator based front view imaging probe seen in FIG. 6a.

FIG. 6f is a schematic side view of an alternative embodiment of a fiber actuator based front view imaging probe seen in FIG. 6a.

FIG. 6g is a schematic side view of an alternative embodiment of a fiber actuator based front view imaging probe seen in FIG. 6a.

FIG. 6h is a schematic side view of an alternative embodiment of a fiber actuator based front view imaging probe seen in FIG. 6a.

FIG. 16b illustrates an alternative embodiment of the combined OCT/IVUS imaging probe seen in FIG. 16a.

FIG. 16c illustrates an alternative embodiment of the combined OCT/IVUS imaging probe seen in FIG. 16a.

FIG. 21d is a magnified IVUS image of the image seen in FIG. 21a.

FIG. 23a is a photograph which shows the imaging location within a white rectangle area on the thigh of the volunteer. The scale bars in FIG. 23a represent 1 mm.

FIG. 23b is a maximum intensity projections (MIP) of the Doppler OCT images of microcirculation network at of human skin at a depth of 120 µm-360 µm.

FIG. 23c is a maximum intensity projections (MIP) of the Doppler OCT images of microcirculation network at of human skin at a depth of 360 µm-600 µm. The arrows indicate new blood vessels detected in each image, and the circles indicate new branches detected in the image.

FIG. 23d is a maximum intensity projections (MIP) of the Doppler OCT images of microcirculation network at of human skin at a depth of 600 μm-840 μm. The arrows indicate new blood vessels detected in each image, and the circles indicate new branches detected in the image.

FIG. 23e is a maximum intensity projections (MIP) of the Doppler OCT images of microcirculation network at of human skin at a depth of 840 μm-1.3 mm. The arrows indicate new blood vessels detected in each image, and the circles indicate new branches detected in the image.

FIG. 23f is an MIP view of the Doppler OCT image at a depth of 120 μm-360 μm.

FIG. 23g is an MIP view of the Doppler OCT image at a depth of 360 μm-1300 μm.

FIG. 26a is an exemplary illustration of a PS OCT intensity image of swine tendon. The scale bar is 250 μm.

FIG. 26b is an exemplary illustration of a PS OCT phase retardation image of swine tendon. The scale bar is 250 μm.

FIG. 27 is a side cross sectional view of a cryoprobe with an integrated OCT catheter.

The disclosure and its various embodiments can now be better understood by turning to the following detailed description of the preferred embodiments which are presented as illustrated examples of the embodiments defined in the claims. It is expressly understood that the embodiments as defined by the claims may be broader than the illustrated embodiments described below.

DETAILED DESCRIPTION OF THE PREFERRED EMBODIMENTS

The disclosed multimodal system for the diagnosis and treatment of cancer and cardiac disease combines thermal therapy with tomographic imaging and thermal imaging guidance to provide accurate diagnosis and treatment of cancer and cardiac disease. With the help of several low cost imaging modalities, such as optical coherence tomography (OCT), ultrasound imaging, photoacoustic (PA) imaging, fluorescence imaging and thermal imaging, thermal therapy can be performed with much higher accuracy. The illustrated embodiment is employed in the following fields.

Figure 1:
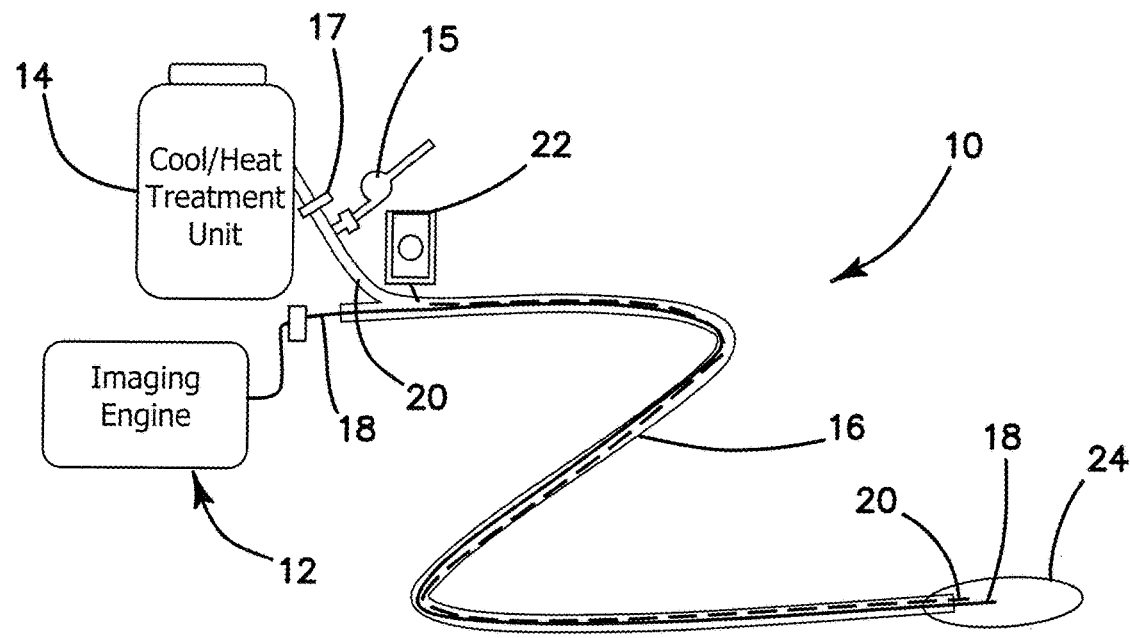
FIG. 1 is a schematic diagram of intravascular diagnosis and therapy system.

As shown in FIG. 1, the multimodal diagnosis and therapy system, generally denoted by reference numeral 10, includes an imaging system 12 and a cooling and/or heating unit or thermoplasty system 14. The imaging system 12 may include several imaging modualities such as OCT, ultrasound, photoacoustic, fluorescence and thermal imaging. These imaging moduailities can also be integrated into a single catheter 16. The imaging catheter 16 and the cryoplasty delivery duct 20 can be integrated into a single structure or catheter 16. The imaging probe 18 could be disposed inside the cryplasty delivery duct 20 or disposed parallel to the cryoplasty delivery duct 20, and both of them would be inside another protective tube or catheter 16. Both the imaging probe 18 and cryoplasty delivery duct 20 may lead to an inflatable balloon 24 at the distal end of catheter 16. In traditional cryotherapy, the cooling process is not monitored. In this embodiment, the imaging system 12 can also be used to monitor the cooling process. The monitoring process can be performed from the structure change, temperature distribution and the OCT functional extension. Cryogenic cooling will induce tissue deformation, because tissue typically shrinks when cooled. Under sufficiently slow cooling rates, freezing occurs in the extracellular space and the cells attempt to maintain equilibrium with the extracellular solution by osmosis. When cells are exposed to the high extracellular solute concentration during slow cooling, the cells shrink. This embodiment uses an endo-thermal camera system 22 to measure or monitor the temperature distribution and monitor the treatment process. In addition, tomographic imaging system 12, such as OCT, ultrasound and photoacoustic imaging, is integrated to monitor the tissue changes in depth direction.

For a large deformation, the change can be visualized directly from the tomographic image. In addition, functional extension of tomographic imaging, such as Doppler OCT/US/PA and its extension, can monitor and analyze a tissue's local or global micro-movement to measure the velocity of moving components in the sample. Subtle changes in tissues can be monitored by Doppler OCT and polarization sensitive OCT.

Figure 2:
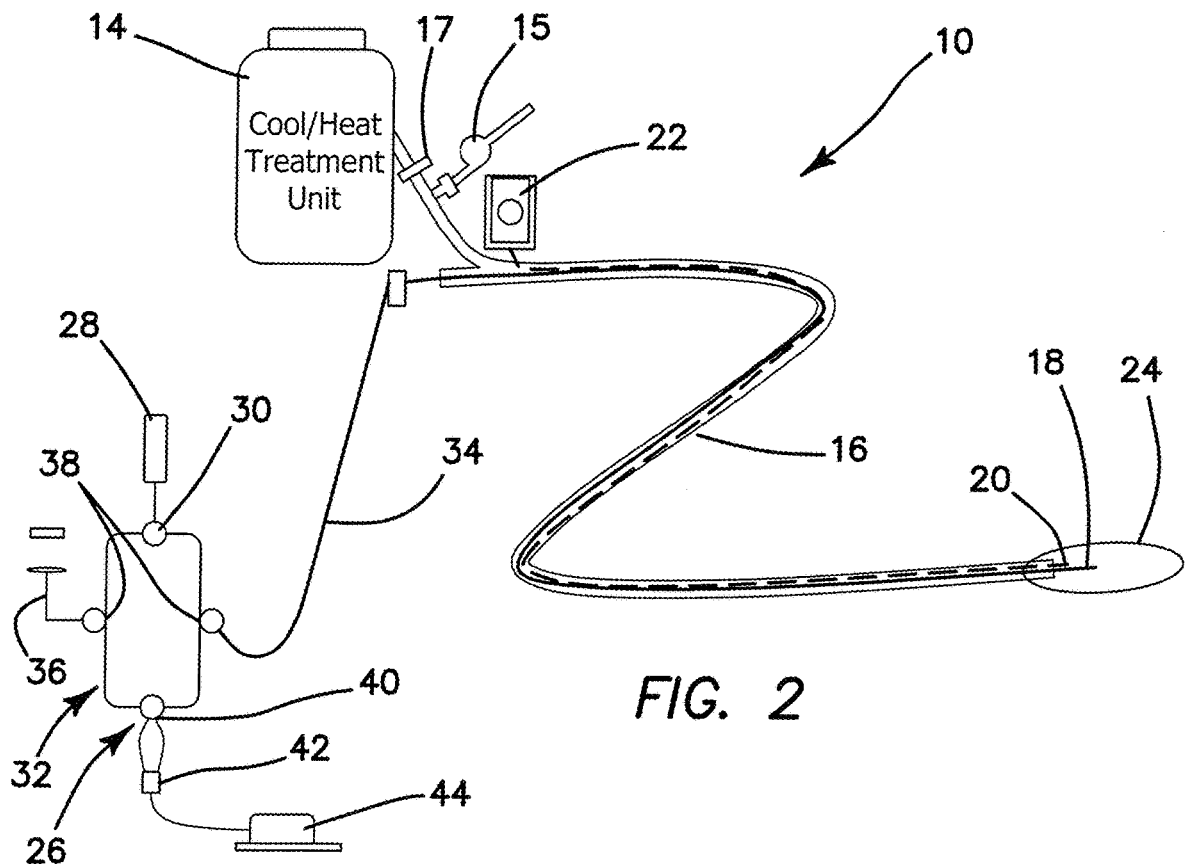
FIG. 2 is a schematic diagram of integrated OCT and thermal therapy system.

OCT System:

In one realization of the system, the imaging system is an OCT system as illustrated in FIG. 2. The OCT system 26 includes a swept source laser 28 with a central wavelength of around 1310 nm. The light from the laser source 28 is split into reference and sample arms by a 1×2 fiber coupler 30. A Mach-Zehnder type interferometer setup 32 may be used, and 90% of the laser light power is sent to the sample arm 34 and 10% of the light to the reference arm 36. Two optical circulators 38 are used in both the sample and reference arms 34, 36 to redirect backscattered and back reflected light to the two input ports of a 50:50 2×2 coupler 40 for detection by detector 42. The detected OCT signal is digitized by a high speed digitizer in a computer 44. In the sample arm 34, a miniature fiber optical OCT probe 18 is packaged in the catheter 16.

Figure 3:
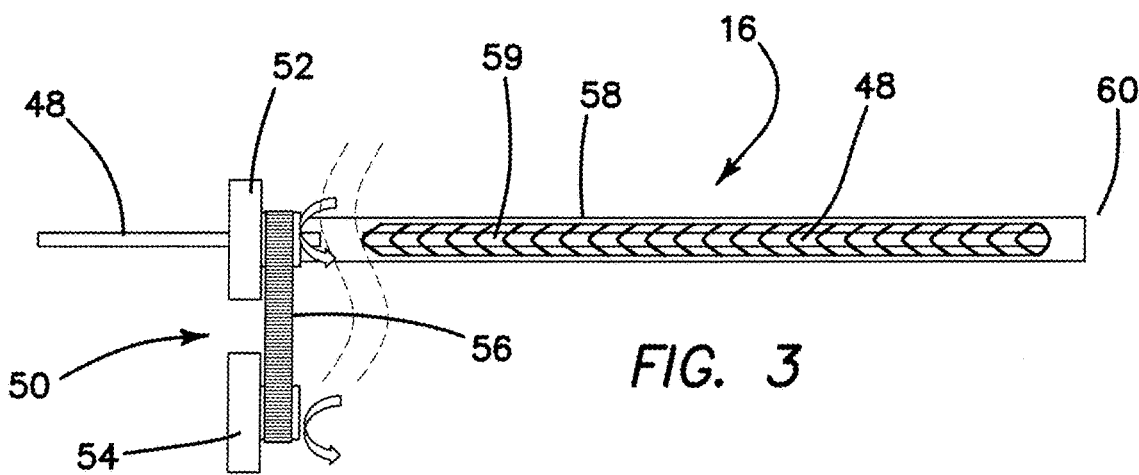
FIG. 3 is a schematic side cross sectional diagram of scanning and imaging catheter.

FIG. 3 shows the enlarged view of the catheter 16. The catheter 16 uses a single mode optical fiber 48 as the light guiding media. A typical single optical fiber has ultralow propagation loss and a very small diameter (250 micrometers, including buffer). OCT imaging requires the scanning of a light beam. The side view probe and forward view probe are used to scan by different methods. For the side view probe, in order to maintain the required small size for intratubular organs, such as vessels, airway, esophagus and colon, an external mechanical scanning device is usually adopted. Rotational scanning of the fiber OCT probe 18 is achieved via a rotational scanning device 50. An external rotational device such as a rotary fiber joint 52 may be used. The rotary fiber joint 52 includes a rotational motor 54 coupled by a belt 56 to fiber joint 52 to enable transmission of optical signals between the rotary and stationary parts of the catheter 16. The fiber 48 is inserted into a torque transmission coil 59 which can transmit the rotation from the fiber's proximal end to its distal end accurately and uniformly. A linear external motor (not shown) is used to pull back the probe or catheter 16 so that a longitudinal circumferential three-dimensional scanning pattern is realized. Because the scanning or imaging engine 12 is located at the proximal end of the probe/catheter 18, 16, which will be inserted into the body of the imaged subject or patient, the probe/catheter 18, 16 can be as small as several hundred micrometers and be used for neural endovascular imaging. At the distal end of the fiber 48, miniature light focusing and re-directing components are used in order to get a high quality OCT image. A gradient index (GRIN) lens (not shown) may be used to focus the light beam and a micro-prism (not shown) is used to direct light in a beam perpendicular to the longitudinal axis of the fiber 48. The whole probe is packaged in a transparent tube 58 to protect the optical elements and the distal tip 60 from mechanical damage.

Figure 4A:
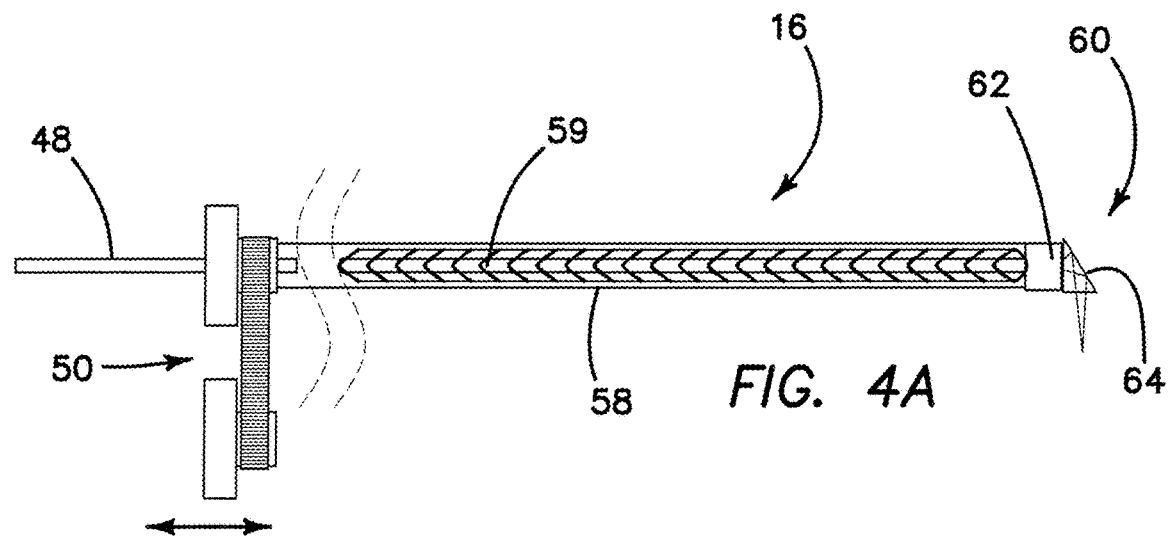
FIG. 4a is a schematic side cross sectional view of one embodiment of a fiber rotatory joint (FRJ) based sized view rotational imaging catheter probe.
Figure 4B:
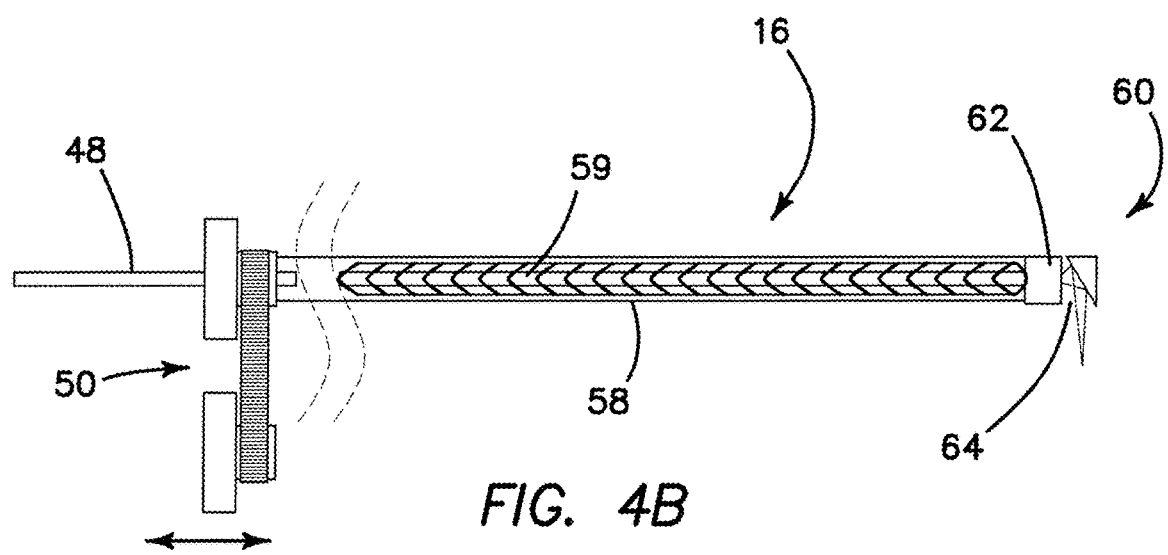
Figure 4C:
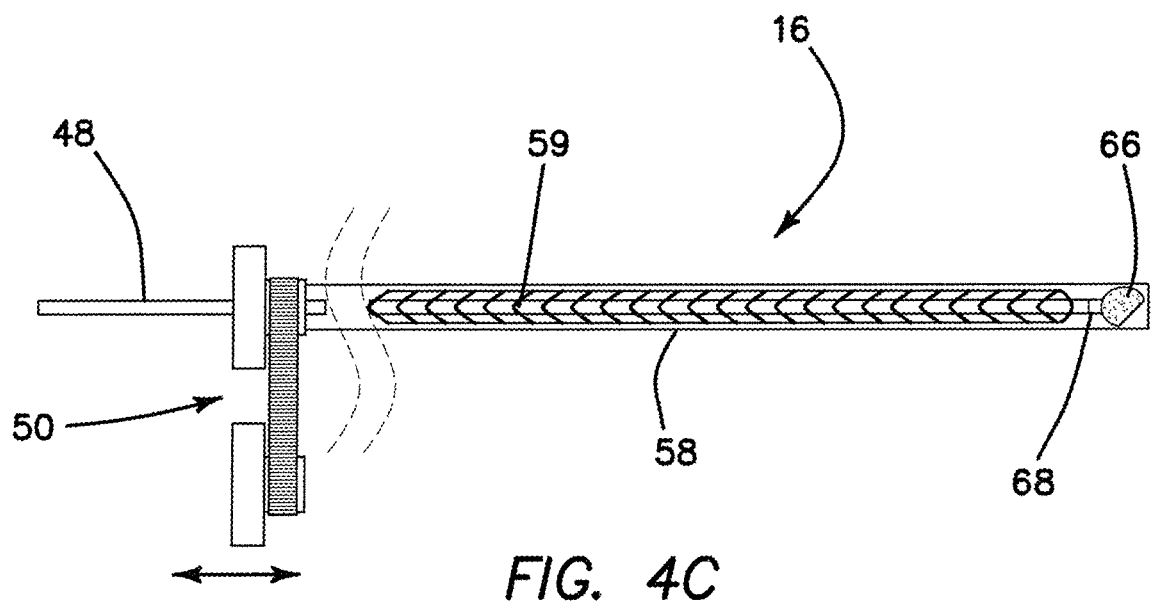
Figure 4D:
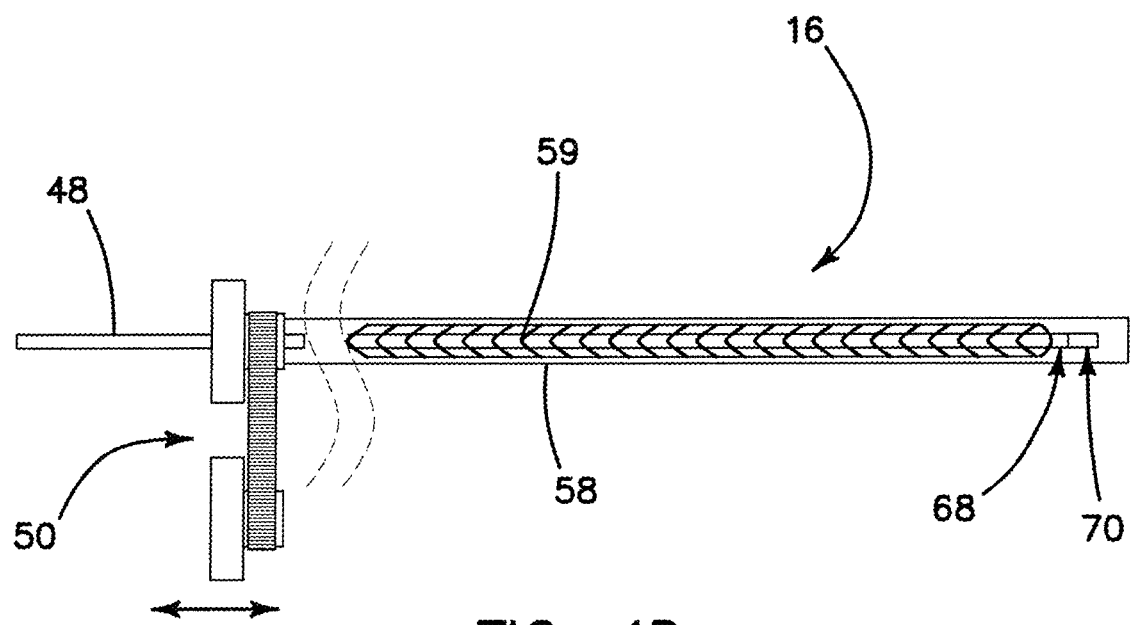
Figure 5A:
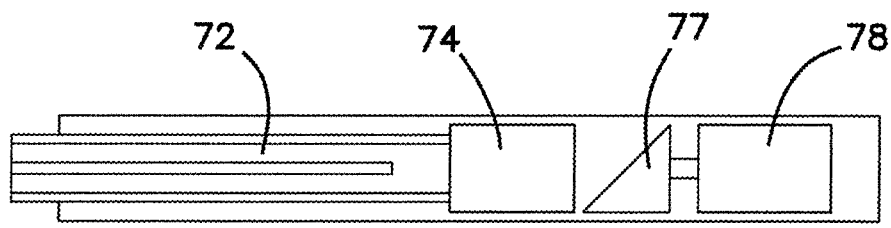
FIG. 5a is a schematic side view of one embodiment of a MEMS-motor based sized view rotational imaging probe.
Figure 5B:
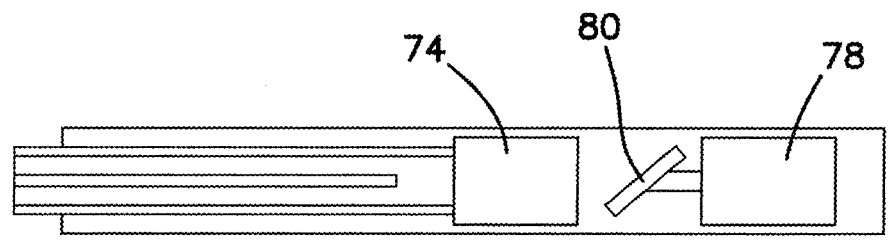
Figure 5C:
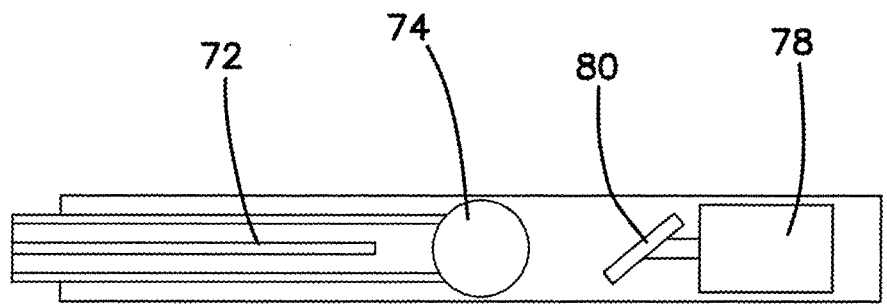
Figure 5D:
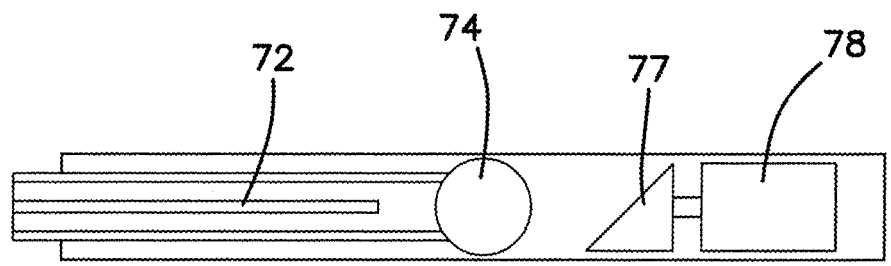
Figure 6A:
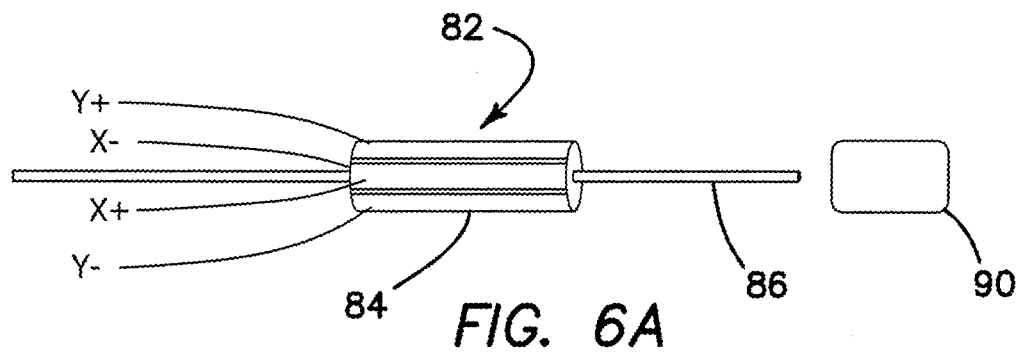
FIG. 6a is a schematic side view of one embodiment of a fiber actuator based front view imaging probe.
Figure 6B:
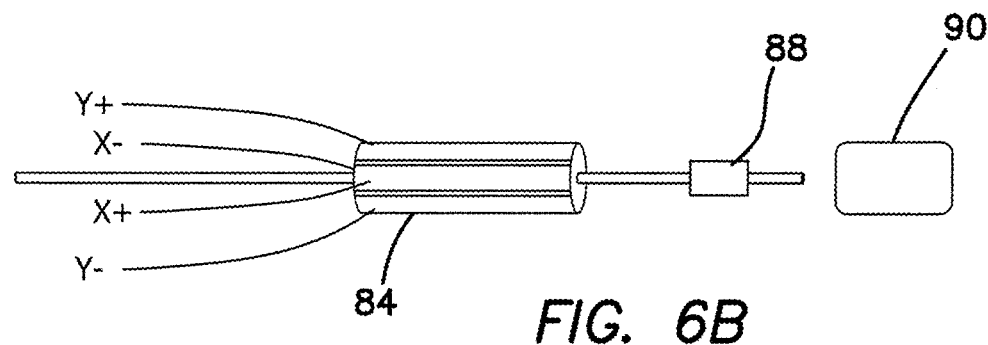
Figure 6C:
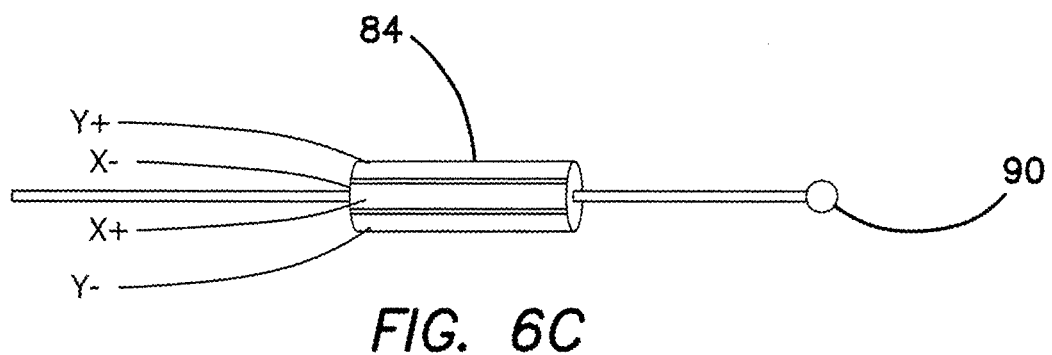
Figure 6D:
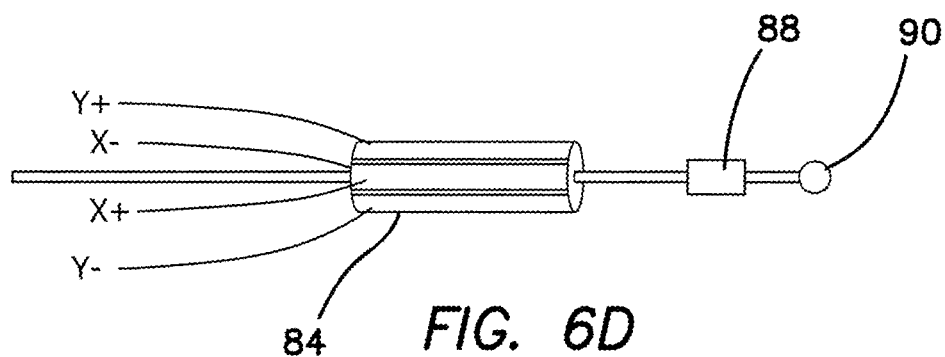
Figure 6E:
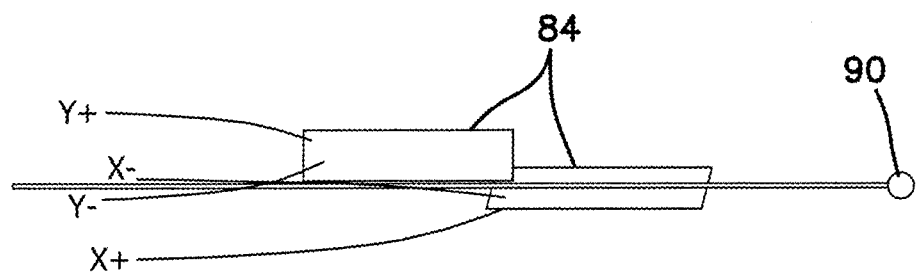
Figure 6F:
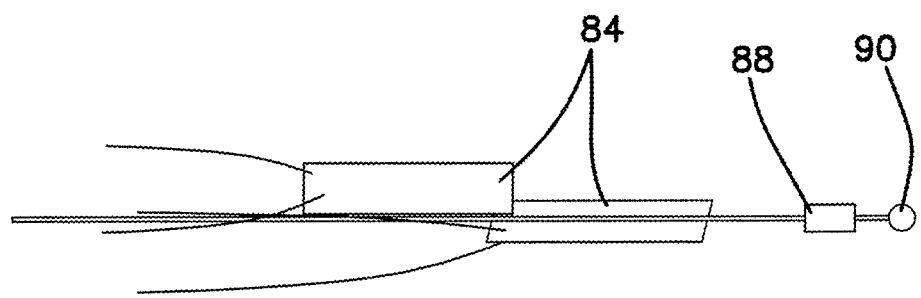
Figure 6G:
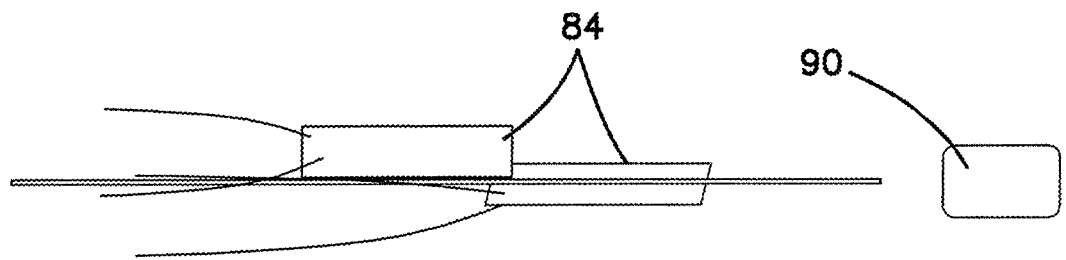
Figure 6H:
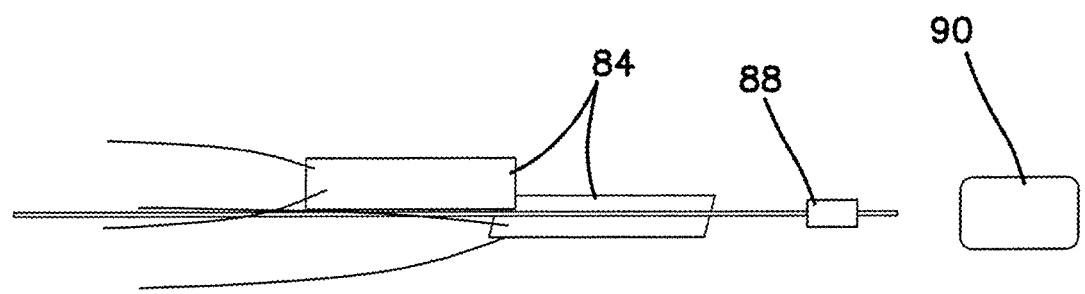

FIGS. 4a-4b show other embodiments of the probe distal-end tip 60. FIG. 4a illustrates tip 60 provided with GRIN lens 62 optically coupling through a perpendicular face of a micro-prism 64 to produce a side scanning beam. FIG. 4b illustrates tip 60 provided with GRIN lens 62 optically coupling through a inclined face of a micro-prism 64 to produce a side scanning beam. FIGS. 4c and 4d illustrate embodiments where Instead of using the GRIN lens 62 and micro-prism 64, full fiber probes are used. One embodiment of a full-fiber probe 18 is to use a ball lens 66 as light focusing component as shown in FIG. 4c. The probe 18 is fabricated by fusing the single mode fiber 48 to a short piece of no-core fiber 68 (spacer); then a ball 66 is made by thermally fusing the tip of the no-core fiber 68 and appropriately setting the fusion splicer parameters. The desired focusing parameters such as focusing spot size and focusing length (working distance), can be tuned by the length of the no-core fiber 68 and the diameter of the fiber ball 66. The fiber ball 66 has a polished flat surface segment at a 45-55 degree angle to redirect the light beam to a direction perpendicular to the longitudinal axis of the fiber. Reflective coating may be used to more effectively redirect light. Similar to the embodiment of FIG. 4c of the full-fiber probe 18, using the GRIN fiber 70 as the light focusing component may also be applied to make a full fiber probe 18 as shown in FIG. 4d. The probe 18 can be made by fusing a single mode fiber 68 to another short piece of GRIN fiber 70. The desired focusing parameters can be tuned by the length of the no-core fiber 68 and lens of the GRIN fiber 70. Again, an angle polish and/or coating may be applied to redirect the light beam for the side view design.

Another embodiment of a scanning side view probe is distal end rotation using a micro MEMS motor. FIGS. 5a-5d show several embodiments of the MEMS motor-based probes 18. In each of the embodiments a light guiding media or fiber optic 72 is optically coupled to focusing optics, such as some type of GRIN lens 74 or ball lens 76, and thence to a beam directing device, such as a prism 77 or mirror 80, coupled to and rotated by a distally mounted MEMS motor 78 in some type of combination thereof. The major advantage of the MEMS motor-based endoscope 16 is that coupling the rotation torque from the proximal end of the traditional endoscope is not necessary. The aluminum-coated prism 77 or mirror 80 is the sole moving part in achieving a 360 degrees full circular view. Because either a lightweight micro-prism/mirror 77, 80 or a 45 degree cut in the fiber optic shaft 72 can be used to deflect the light, a real time frame rate (>50 frames/second) is achieved easily by the MEMS motor's output torque. Since rotation of the entire endoscope 16 is eliminated, a metal reinforcement sheath in the distally rotated endoscope design is no longer needed. Hence, endoscope flexibility is increased. In addition, the fiber rotary joint 50 (FRJ) between the traditional rotational endoscope 16 and static sample arm fiber 34 is unnecessary and, thus, coupling power fluctuations are decreased.

Another kind of probe 18 is a forward view cantilever type scanning probe 18. FIGS. 6a-6d show eight embodiments of forward view imaging probes 18. Among various types of forward-view imaging OCT catheters, a cantilever scanner includes a fiber cantilever 82 which is oscillated by a quartered actuator 84. The optic fiber used in the OCT is quartered to give Y+, Y−, X+, and X− fiber segments. In spite of the inherently small displacement of such a small actuator 84 of each fiber segment (a few micrometers at best), a large scan amplitude can be obtained by the resonant oscillation of the fiber cantilever 82. A two dimensional scan can be achieved by modulating the amplitude of the two pairs of actuation signals combined with the two dimensional resonant oscillation. A spiral scan strategy has been used to obtain three dimensional OCT tomograms, which is obtained by an amplitude modulation. A circular scan pattern of the fiber end sweeps the area with a varying radius in this scan strategy. A piezotube actuator 84 is relatively compact (<10 mm$^3$) and has a cylindrical geometry, which is compatible with the typical cylindrical shape of a catheter 16. It can be easily assembled in a simple and robust configuration in a miniaturized OCT catheter 16. These scanning probes 18 are driven by either piezoelectric, electrostatic or magnetic force. The driving material can be lead zirconate titanate (PZT), deformable polymer or other materials depending on the driving force as are well known to the art.

The scan frequency of the fiber cantilever is determined by its resonance frequency (natural frequency) which is tuned by the properties of the cantilever fiber. The resonance frequency gets lower as the length of the fiber cantilever increases. The embodiments of FIGS. 6a-6d all have equal length fibers for each quarter segment, and the embodiments of FIGS. 6e-6h are split with different length segments in a pairwise fashion, X+ and X−, Y+ and Y−. But the resonance frequency obtainable with a compact cantilever is still far higher than the desired range of the scan frequency in an OCT scanner. It needs to be well below 100 Hz for the typical high-speed spectral-domain OCT (SD-OCT) or swept-source OCT (SS-OCT) systems where the A-line rate is usually below 100,000 lines per second. Further elongation of the fiber cantilever is disadvantageous in terms of compactness. For example, a resonance frequency of 60 Hz is obtained when the length of the cantilever fiber (fused silica) with a standard diameter of 125 μm exceeds 40 mm. This is unacceptably long to make a compact endoscope catheter. The frequency can be reduced by increasing the mass of the oscillating body or by putting a weight 88 at the end of the cantilever as shown in the embodiments of FIGS. 6b, 6d, 6f and 6h. The embodiments of FIGS. 6a, 6b, 6g and 6h have a distal focusing element 90, such as a GRIN lens. The embodiments of FIGS. 6c-6f have a distal focusing element 90, such as a fiber ball lens or GRIN fiber.

For a two dimensional cantilever scanner 82, non-resonant actuation has the advantage of wider freedom of operation, especially for the capability of a simple, but nearly ideal two dimensional raster scan, which requires a far different scan frequency for each axis. The scanning strategy can be resonant, non-resonant or semi-resonant.

Thermal Angioplasty Balloon

Figure 7A:
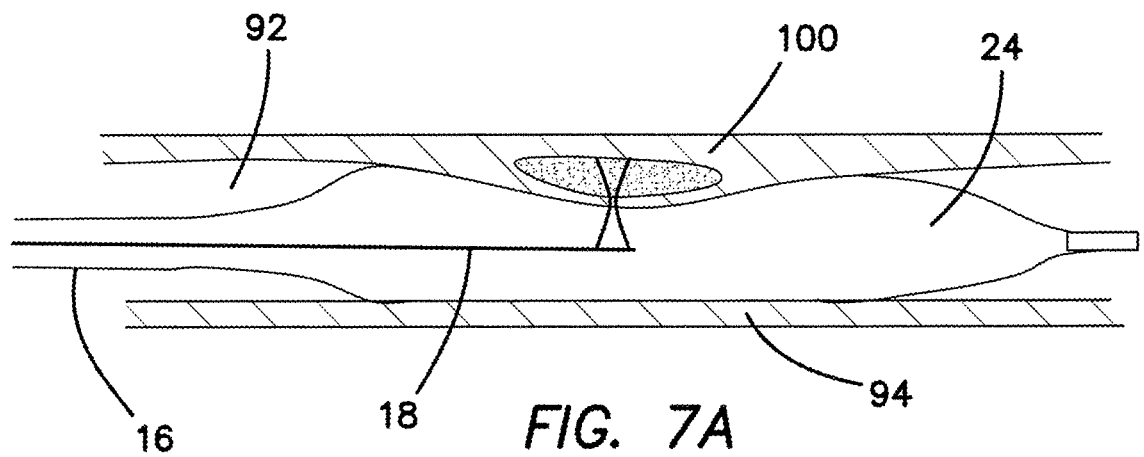
FIG. 7a is a schematic of an embodiment directly combining the cryoplasty balloon with the OCT catheter in an integrated OCT imaging probe and cryotherapy balloon catheter in a blood vessel lumen.
Figure 7B:
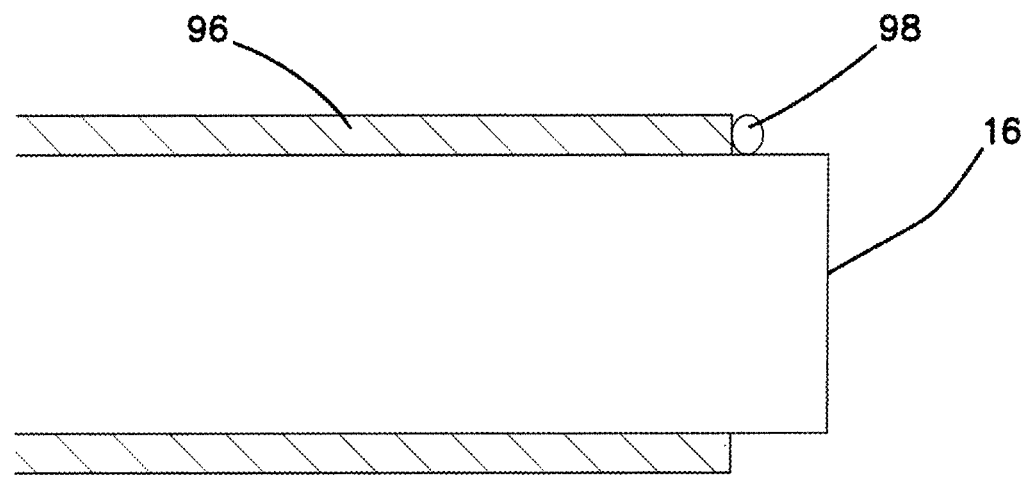
FIG. 7b is an enlargement which illustrates the location of the insulation coating and the thermometer imbedded.

FIGS. 7a-7d show schematics using the integrated OCT imaging catheter 16 and cryotherapy balloon 24 for the diagnosis and treatment of plaque. There are three possible methods realizing the integration. FIG. 7a illustrates a direct combination of the cryo-balloon 24 and the OCT catheter 16. The OCT catheter 16 is introduced into a lumen 92 of the blood vessel 94. There is an insulation layer coating 96 on the OCT catheter 16 and a thermometer 98 imbedded on the surface of the insulation layer 96 monitoring local temperature as illustrated in the right enlarged image in FIG. 7b. The balloon 24 is positioned around the plaque region 100 in the vessel lumen 92. Plagues, plague regions, diseased tissue or tissue regions, tumor tissue, tumor sites and the like will be generally referenced collectively by reference numeral 100 and shall be collectively understood as such. The operator will image the blood vessel walls 94 with OCT, and from the OCT image, the exact location, size, thickness and vulnerability of the plaque region 100 will be judged by physicians. The image in FIG. 7e shows an OCT image of a blood vessel 94 with plaque 100. Depending on the information obtained from the OCT image, cryogenic cooling fluid may be introduced into the balloon 24. The arrows in FIGS. 7c and 7d along the OCT catheter 16 illustrate flow direction of the fluid. The amount of cooling fluid (usually liquid nitrogen or liquid nitrous oxide) and the time for the cooling will also be decided from the analysis of the OCT image and controlled by the valve 17 and pump 15 (shown in FIG. 1 and FIG. 2). During the cooling processes, the operator will continuously acquire OCT images to monitor the treatment process. After freezing, the evaporated cooling agents will be pumped out of the balloon 24.

Figure 7C:
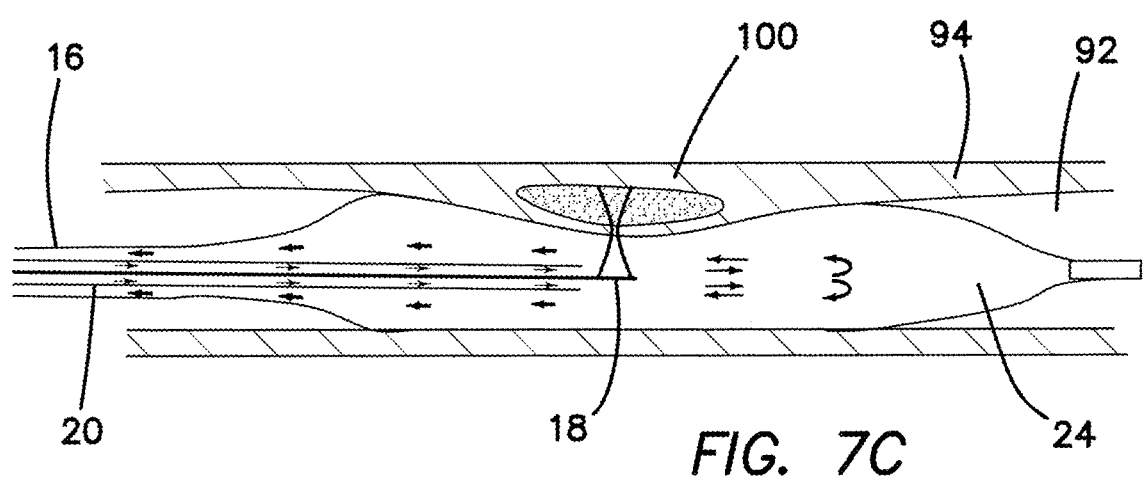
FIG. 7c is a schematic of an inlet tube is used for the cryogenic fluid. The OCT catheter is placed in the middle of the inlet tube.
Figure 7D:
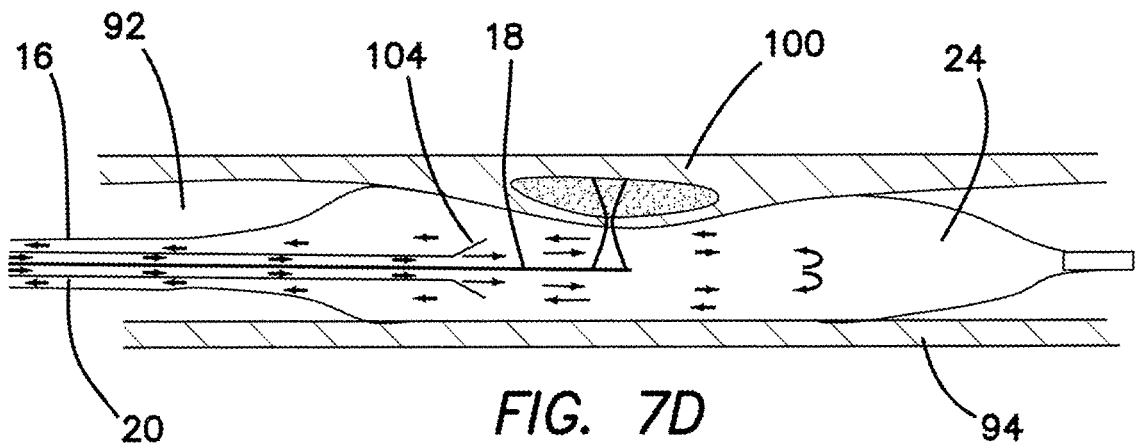
FIG. 7d is a schematic illustrating freezing achieved by a J-T expansion valve.
Figure 7E:
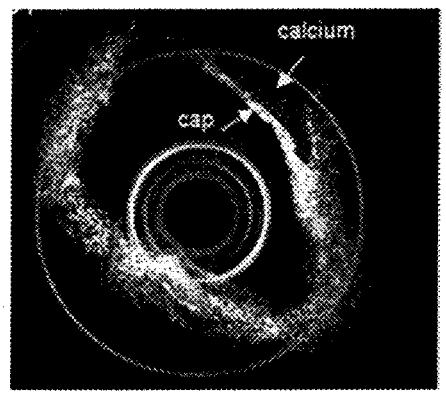
FIG. 7e is an OCT image of a blood vessel with plaque identified by the arrows obtained with the OCT catheter of FIGS. 7a-7d.

For better protection of the healthy tissue, the cryogenic fluid may be introduced through the inlet tube 20 as shown in FIGS. 7c and 7d, the relative position of the tube 20 to the OCT catheter 16 is adjusted according to the imaging diagnosis of the OCT. The adjusted outlet of the tube 20 should be near the proximal end of the plaque 100. The small arrows illustrate the flow direction of the liquid agents, and the liquid may evaporate into the gas after exchange heat with the surrounding plaque 100, and the enlarged arrows illustrate the flow in gas phase. The flow rate can be also controlled by the valve 17 and the pump 15.

Freezing may also be achieved by using a J-T expansion valve 104 in which the argon gas of room temperature is delivered to the balloon 24 through the tube 012, and it expands adiabatically and results in liquid argon, shown in FIG. 7d. The liquid argon will evaporate and inflate the balloon 24 while freezing the surrounding targeted tissue 100. By controlling the flow rate of the argon, the freezing rate could be controlled according to the therapeutic requirements.

Figure 8:
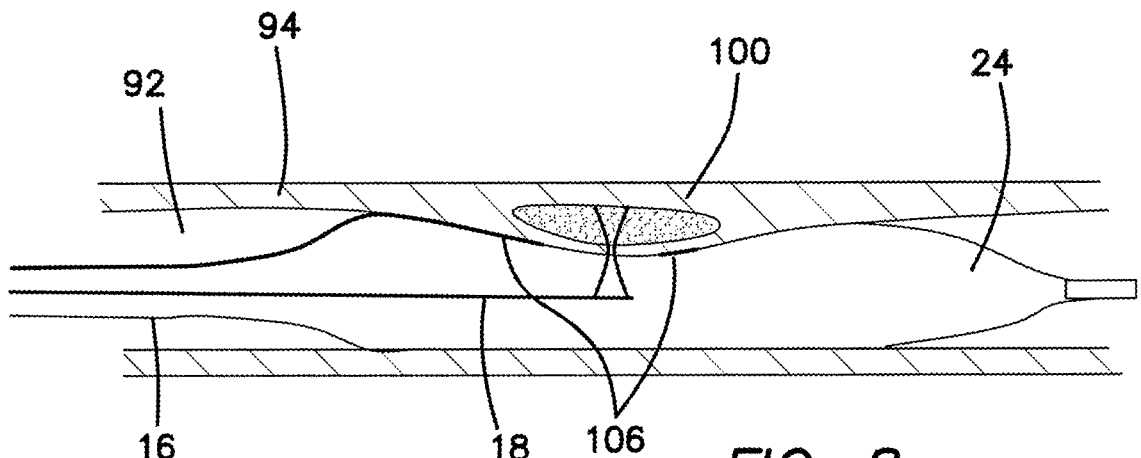
FIG. 8 is a schematic diagram of an integrated OCT imaging probe and RF thermal angioplasty balloon catheter in a blood vessel lumen. The RF electrodes are on the surface of the balloon.

FIG. 8 illustrates the integrated OCT imaging catheter 16 and thermal-plasty balloon 24 for the diagnosis and treatment of the plaque 100. It uses RF to heat the treatment domain or plaque 100. The RF electrodes 106 are on the surface of the balloon 24, and they are connected to the RF generator (not shown) and the control board (not shown) by the flexible wires imbedded in the catheter 16. When the plaque 100 is diagnosed as treatable and treatment domain determined by the integrated imaging system 12, planned radiofrequency heating by the electrodes 106 can be started. The radio frequency energy penetrates into the plaque 100 and results in high temperature killing the proliferated smooth muscle cells and damage the diseased tissue. Inside the balloon 24, there can be flow at certain temperature to protect overheating of the vascular endothelium. The temperature of the circulation flow inside the balloon 24 can be adjusted together with the radio frequency heating power for a complete ablation of the plaque 100 while sparing the endothelium.

Figure 9A:
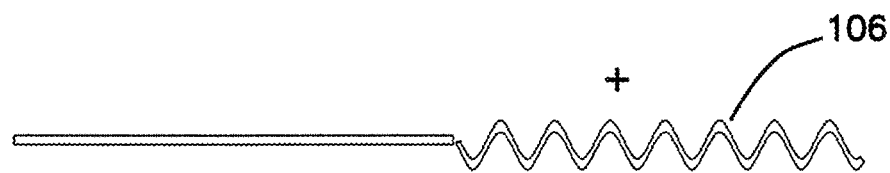
FIG. 9a illustrates one single electrode or unipolar electrode embodiment for RF emission.
Figure 9B:
FIG. 9b illustrates a bipolar electrode embodiment for RF emission.

The radiofrequency electrodes 106 on the balloon surface can either be a design of one single positive electrode 106 in FIG. 9a or bipolar electrodes 106 in FIG. 9b. Unlike the bipolar electrode setup, in which two electrodes 106 are used, where one is positive and the other one is negative, the single electrode design as shown in FIG. 9a, the electrode 106 itself is the positive electrode, and the surrounding tissue serves as the negative electrode.

Figure 10A:
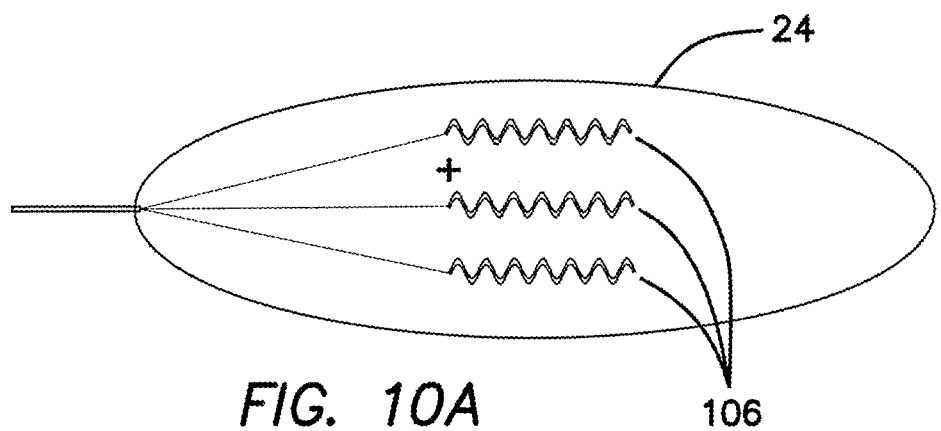
FIG. 10a illustrates an embodiment of multiple RF electrodes on the surface of the balloon comprising multiple positive electrodes made of coils.
Figure 10B:
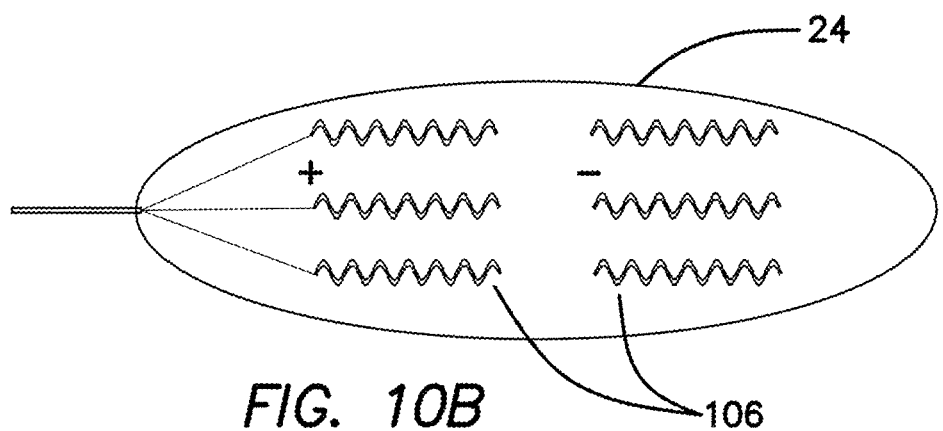
FIG. 10b illustrates an alternative embodiment of multiple RF electrodes on the surface of the balloon comprising multiple biopolar electrodes made of coils.
Figure 10C:
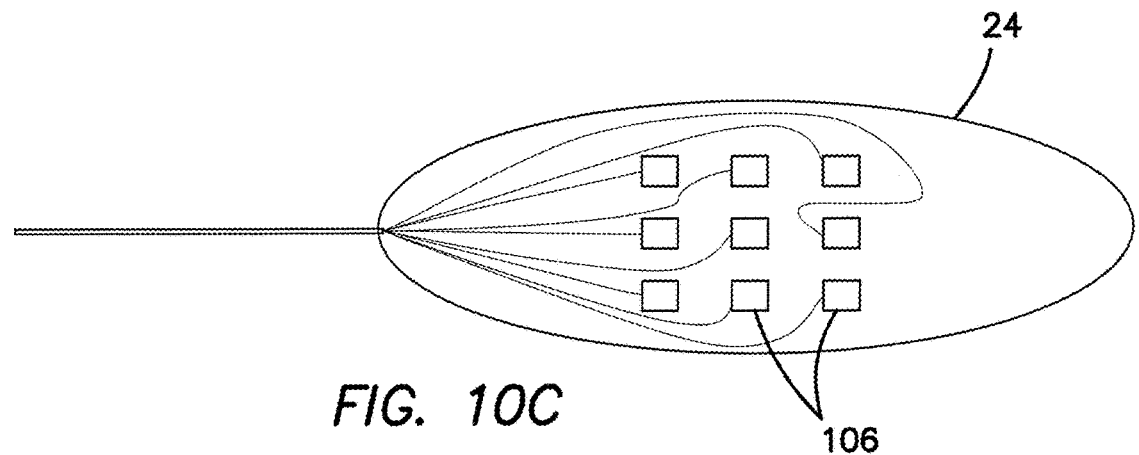
FIG. 10c illustrates an alternative embodiment of multiple RF electrodes on the surface of the balloon comprising electrodes made of metal or semiconductor films.

As shown in FIGS. 10a-10c radiofrequency heating can be realized by multiple electrodes 106 with each electrode 106 being separately controlled to cover the treatment domain while sparing the healthy tissue. The electrodes 106 can be resistive coils as in FIGS. 10a and 10b or thin metal or semiconductor films as in FIG. 10c.

Figure 11:
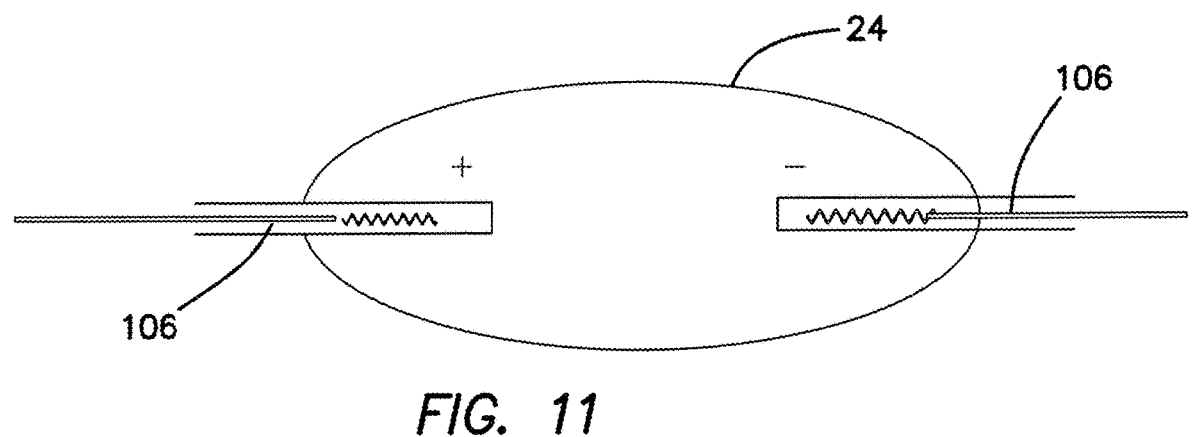
FIG. 11 is a schematic diagram which shows the RF electrodes are inside the balloon.

The radiofrequency electrodes 106 can be manufactured inside the balloon 24 as shown in FIG. 11. With the RF electrodes 106 inside the balloon 24, the radio frequency energy heats up the surrounding ionic solution and the heated solution heats the surrounding plaque 100.

Figure 12:
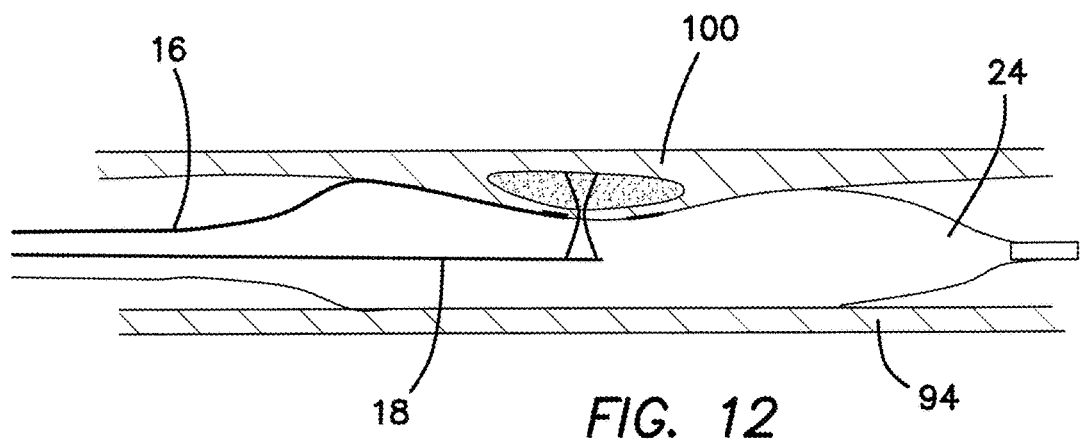
FIG. 12 is a schematic diagram illustrating a microwave antenna on the surface of the balloon.

The heating of the tissue may use microwaves with an antenna 108 on the surface of the balloon 24. As shown in FIG. 12 by connecting the antenna 108 to a microwave generator (not shown), the microwaves are emitted to heat the contacted disease tissue.

Figure 13A:
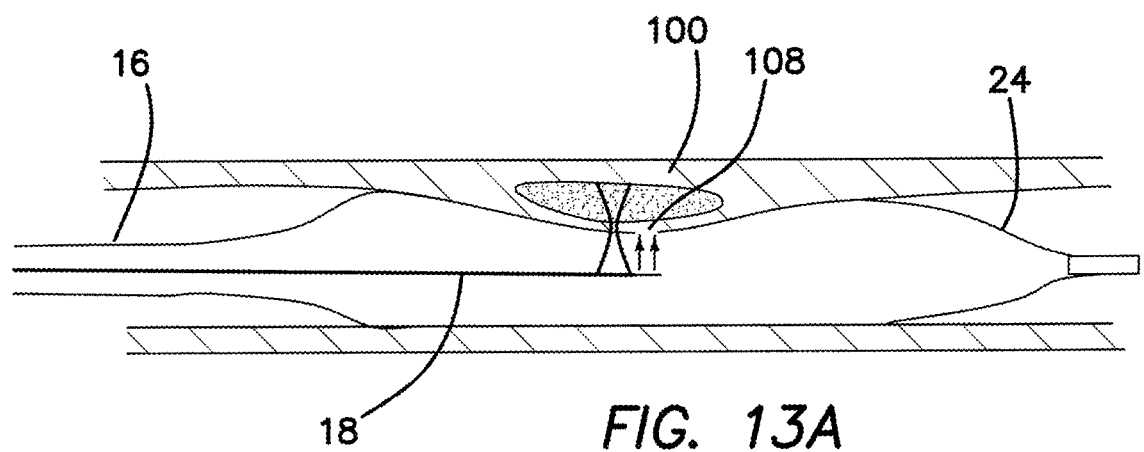
FIG. 13a illustrates the use of choice for the optical fiber location for optical laser/infrared heating, the optical fiber for transmission of light is provided directly from the OCT probe attached to the balloon surface, and there is a transparent window for light transmission through the balloon.
Figure 13B:
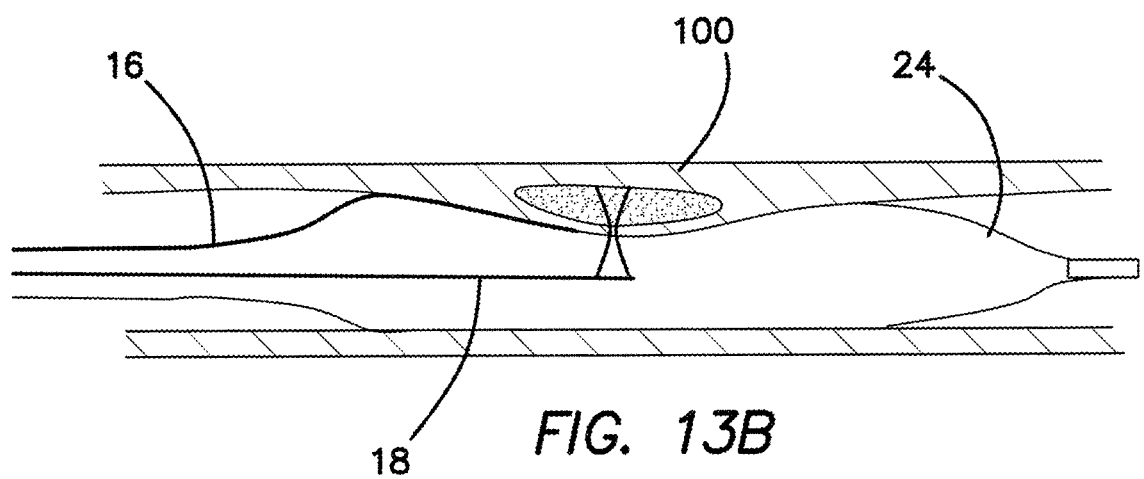
FIG. 13b illustrates the use of choice for the optical fiber location for optical laser/infrared heating, the optical fiber for transmission of light is focused through the balloon from the tip of the probe.

The tissue may be heated using an infrared or optical laser. As shown in FIGS. 13a and 13b, the laser or Infrared light for ablation of the plaque 100 is conducted to the diseased region or plaque 100 through fiber optics. The fibers may be attached to the surface of the balloon 24 as shown in FIG. 13a, or be aligned or focused with the OCT lens as shown in FIG. 13b. After the treatment domain is decided by OCT imaging, the laser or infrared light is transmitted to the exact place desired for ablation of the tissue.

Combined Heating and Cooling:

i. The heating protocols and devices as illustrated in FIGS. 8-13b and freezing protocols and devices as illustrated in FIG. 7a-7e of the tissue can be used alternatively for improved killing or tumor cells. The heating and cooling of the tissue can be used together for better temperature control and rapid adjustment for more accurate and effective treatment. The heating and cooling can be used together for a specified shape of the ablation region. By carefully planning of the heating zones and cooling zones separately, a special shape of ablated region can be obtained.

Figure 14:
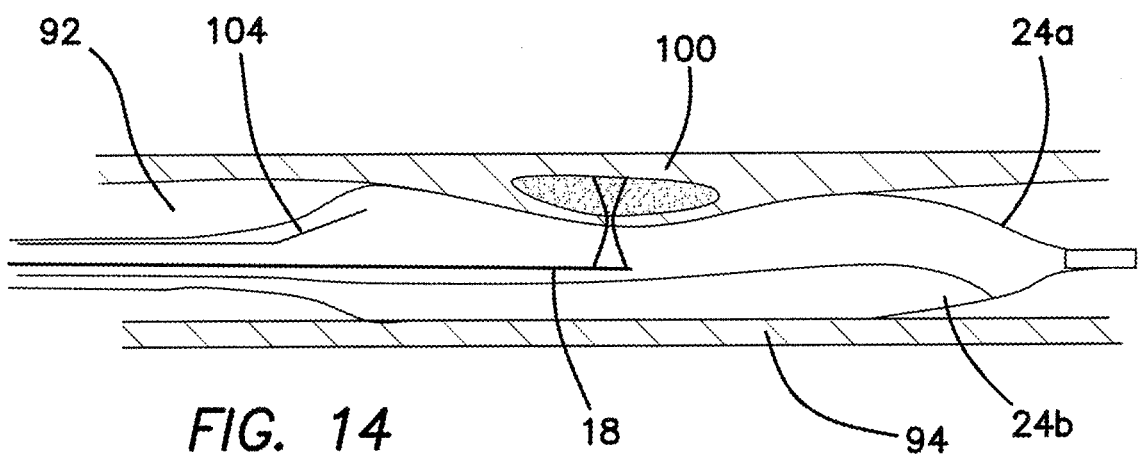
FIG. 14 is a schematic diagram of an integrated OCT imaging probe and dual balloons catheter in a blood vessel lumen.
Figure 15:
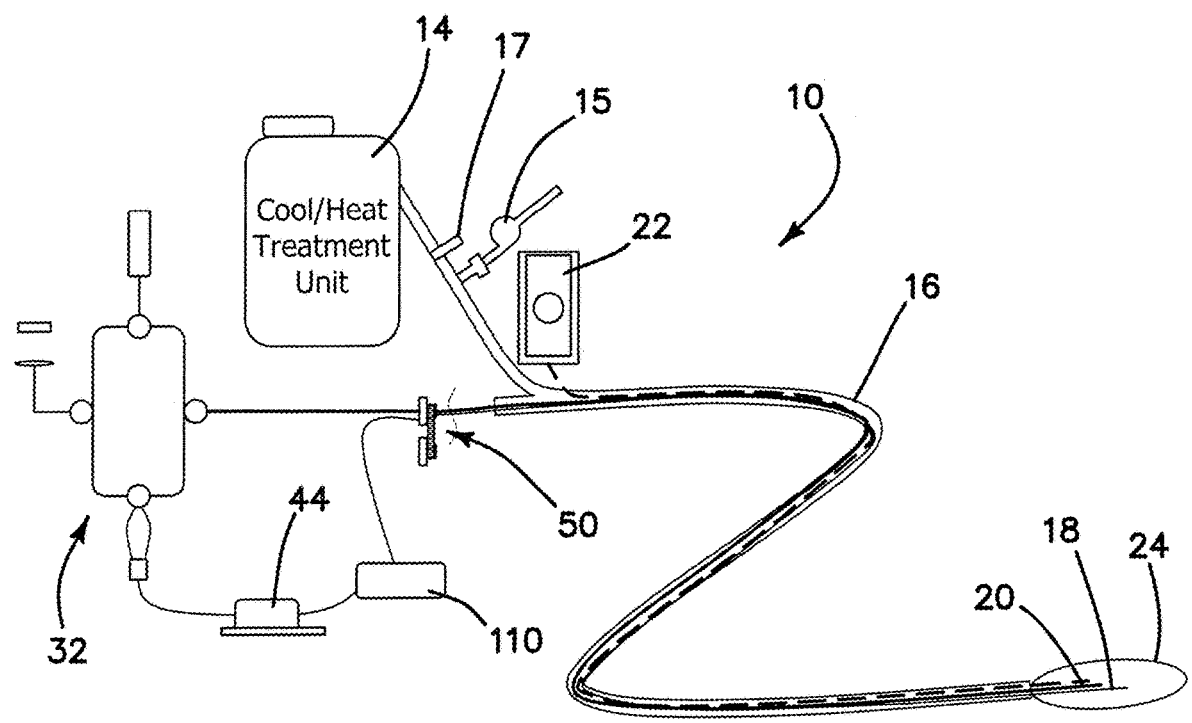
FIG. 15 is a schematic of an integrated OCT/IVUS and cryotherapy catheter system.

Multiple Balloons Design:

The integrated catheter 16 may further adopt dual or multiple balloons 24a, 24b. FIG. 14 shows the schematic of the dual balloon catheter 16 inside a blood vessel lumen 92. The dual balloons longitudinally divide the interior space of catheter 16. Any division or compartmentalization of subspaces within the volume normally occupied by balloon 24 is included within the scope and spirit of the invention and three or more nonlongitudinal divisions is expressly contemplated. Both/all balloons 24a, 24b are connected to a cryogenic cooling liquid tank (not shown) and another normal temperature gas/air tank (not shown) in cooling/heating treatment unit 14; however, only one will be filled with cryogenic cooling liquid during the treatment. OCT will be used to identify the location of the plaque 100. Once the plaque region 100 is identified, one of the balloons 24a or 24b, which touches the plaque 100, will be filled with cryogenic cooling liquid and the other one of the balloons 24b or 24a will be filled with normal temperature gas or air. In this way, only the plaque region 100 will be treated and the surrounding healthy region will not be affected by the cryotherapy. This arrangement greatly enhances treatment efficiency and reduces side effects caused by cryotherapy. This improvement can only be realized with the help of imaging techniques such as OCT which can accurately identify the plaque location 100.

IVUS-OCT System:

OCT & IVUS provide structural imaging at two different length scales. For some applications, only OCT alone cannot visualize the entire region of interest due to its limited penetration depth, ~1.5 mm. 30 MHz IVUS can image over 5 mm deep inside the tissue to cover the full thickness of the plaques 100 and the entire depth of tumor tissue.

For example, in a cardiovascular application, intravascular OCT and US provide complementary information for vascular imaging applications. IVUS can image ~5 mm deep inside the tissue to cover the full thickness of the plaques 100. However, IVUS resolution is on the order of 50 microns to 200 microns which is not enough to resolve the fibrous cap thickness. On the other hand, OCT images provide details at a higher resolution on the order of 5 microns to 20 microns, which can be used to accurately assess the thickness of a plaque fibrous cap. However, OCT has limited imaging depth and cannot quantify the full thickness of the plaque 100. Recently, Sawada et al. studied the feasibility of the combined use of IVUS and OCT data (images acquired separately) for detecting thin-cap fibroatheroma (TCFA) with 56 patients. The results clearly showed that neither modality alone is sufficient for detecting TCFA. The combined use of OCT and IVUS might be a feasible approach for evaluating TCFA. The combined IVUS/OCT system can achieve depth penetration and superior resolution.

Figure 16D:
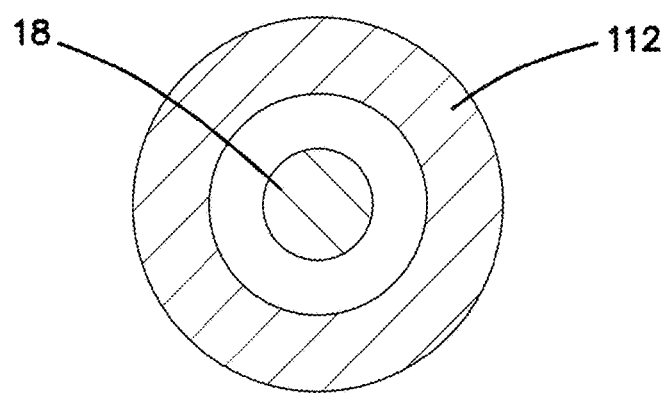
FIG. 16d is a side view of the embodiment of FIG. 16c showing the relative location of oct probe and ultrasound transducer.
Figure 16A:
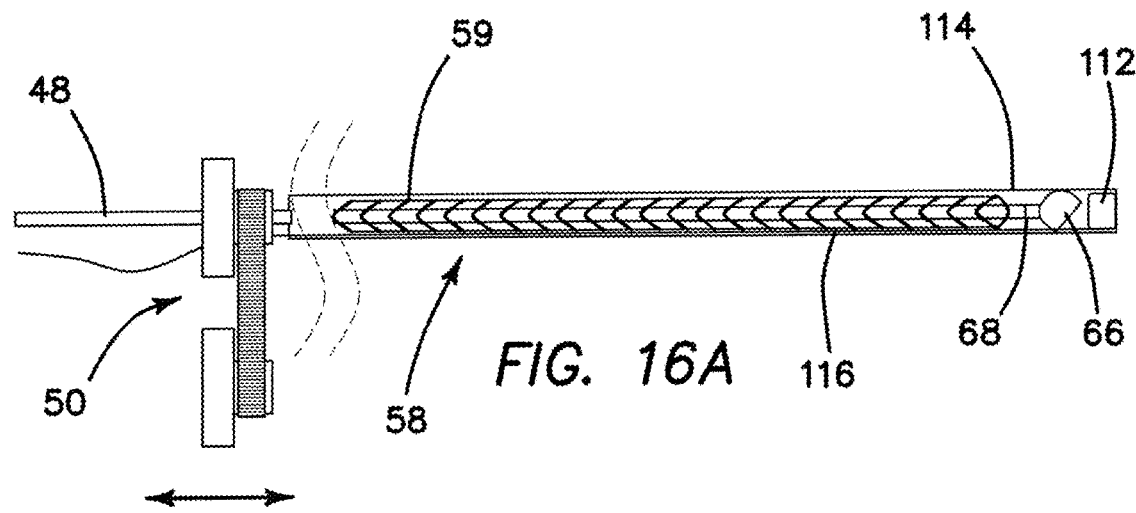
FIG. 16a illustrates an embodiment of the combined OCT/IVUS imaging probe.
Figure 16B:
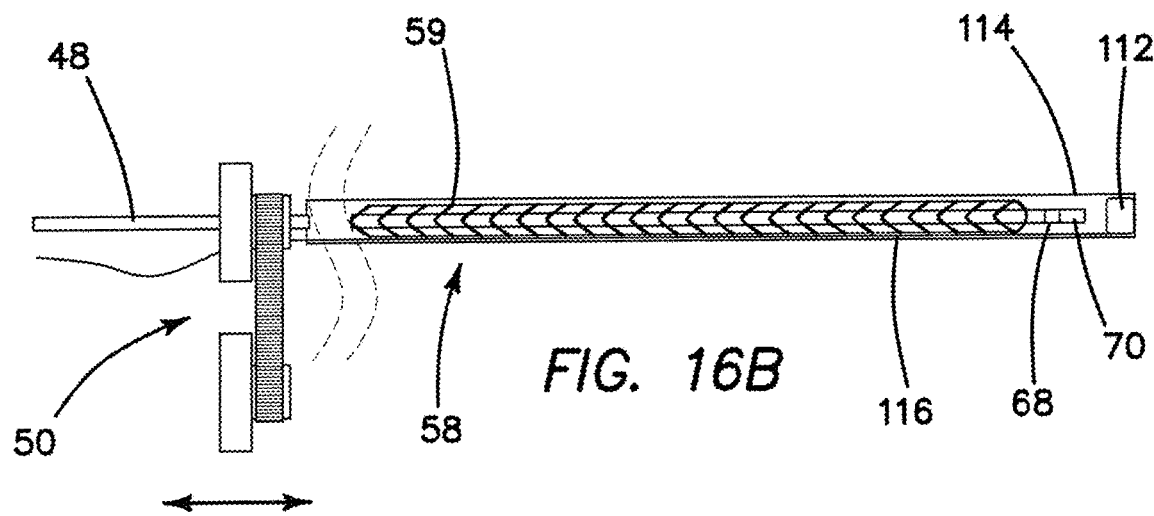
Figure 16C:
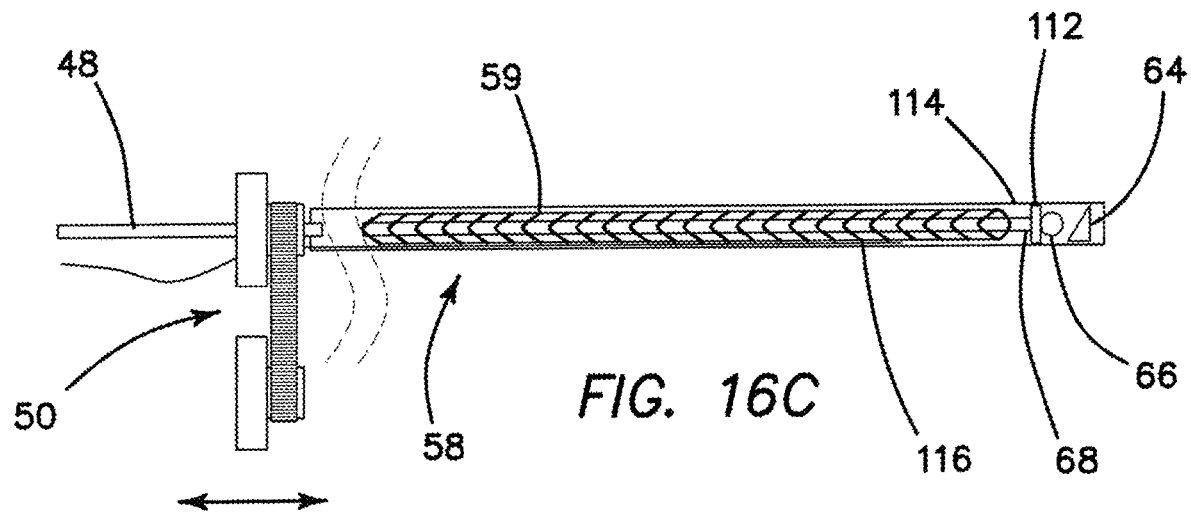

Based on these results, the illustrated embodiments of the invention further include IVUS imaging modality into the system 10 to provide deep tissue monitoring, as shown in FIGS. 16a-16d. Using a micro US transducer 112 coupled through an ultrasound wire 116 to ultrasound pulser/receiver 110 and micro OCT probe 18, the further inclusion of IVUS into the system 10 will not increase the diameter of the catheter 16. Three embodiments of an integrated imaging catheter 16 are shown in FIGS. 16a-16d, where FIG. 16a is a schematic of an OCT probe 18 having a fiber spacer 68 and fiber ball 66 for focusing with a distal US transducer 112; FIG. 16b having a fiber spacer 68 and GRIN fiber lens 70 with a distal US transducer 112; and FIG. 16c having a fiber ball lens 66 and prism/reflector 64 and an US ring transducer 112. FIG. 16d is a schematic plan end view of the distal tip of catheter 16 of FIG. 16c, showing the OCT probe 18 disposed within US ring transducer 112. The OCT probe 18 and the ultrasound transducer 112 are positioned closely to each other. The ultrasonic transducer 112 with an aperture size of around 0.5 mm×0.5 mm can be built using a PMN-PT single crystal or other material, which has superior piezoelectric properties for building high sensitivity US transducers in a small size. Other IVUS probe materials, such as PZT, and other piezoelectric materials may be used. Other IVUS probe designs such as a ring transducer 112 in FIG. 16c or an array (not shown) may also be used. The center frequency of the ultrasound transducer is preferably in the range of 10 MHz-50 MHz, depending on the application. The transducer 112 can be fixed in the distal end of a thin-wall polyimide or metal tube 114 within which the OCT probe 18 is also disposed. A transmission window (not shown) is provided in the tube 114 to let both a light beam and sound wave exit. The inclusion of US will enable one to monitor the effect of a cryogenic cooling or heating process in a deep region of tissue.

Figures 17A, 17B:
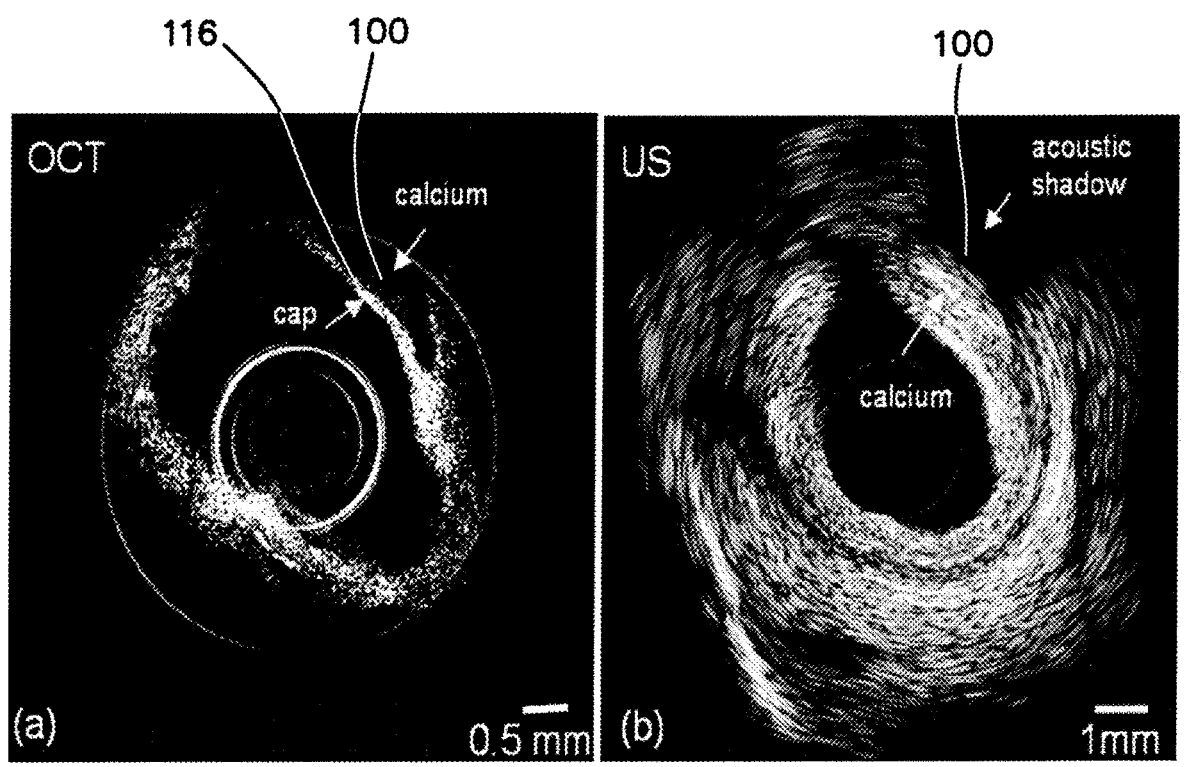
FIG. 17a is an OCT image of a human coronary artery specimen.
FIG. 17b is an image of a human coronary artery specimen.

FIGS. 17a and 17b show the OCT and US images of a human coronary artery specimen with calcified plaque. The plaque 100 can be identified in both images. From the OCT image in FIG. 17a, the plaque cap 116, as highlighted by the arrow, can be clearly identified due to the high axial resolution and high contrast of OCT. However, the OCT system could not visualize the entire depth of the vessel wall, and its maximum penetration depth was about 1 mm. On the other hand, in the US image in FIG. 17b, the acoustic shadow, as pointed by the arrow, indicates the location of the plaque 100. However, one can hardly distinguish the border between calcium and the surrounding tissue due to the inferior resolution of the US, but its penetration depth was much deeper than that of OCT (the radius of the image is 4.5 mm). These disclosed images clearly demonstrate the benefits of the combination of US and OCT for plaque imaging.

Figure 18:
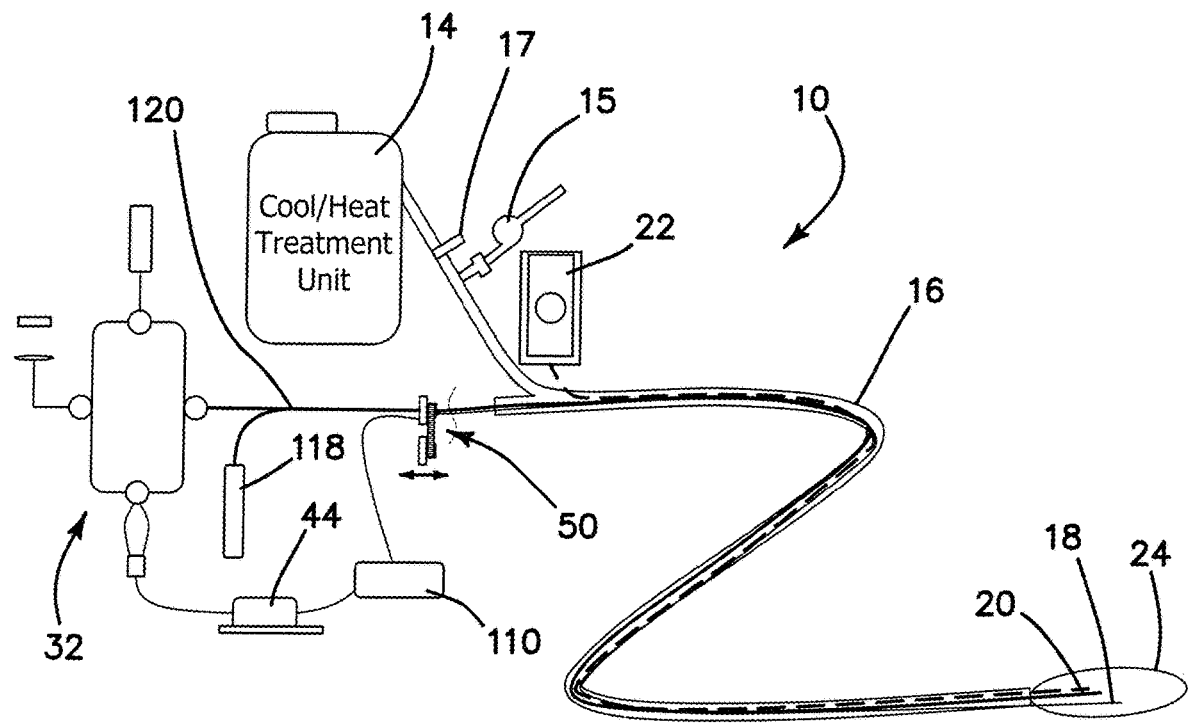
FIG. 18 is a schematic of integrated OCT/PA/IVUS and thermal therapy catheter, with a wavelength division multiplexer, WDM.

IVUS-PA-OCT System:

The embodiments of the invention further include photoacoustics, PA, into the imaging modalities as shown in FIG. 18. A pulsed laser 118 is used as the PA signal excitation source. The free space laser output from laser 118 is focused by an objective lens (not shown) and coupled into optical fiber 48 for delivery through a wavelength division multiplexer, WDM 120. The PA fiber 48s included into the OCT/IVUS catheter 16 without sacrificing the total diameter of the catheter.

Figure 19:
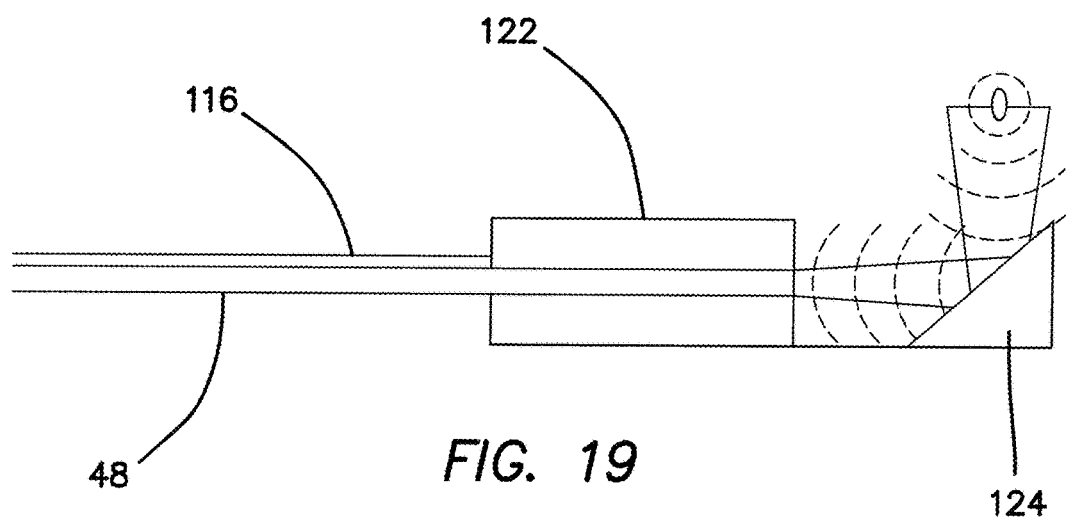
FIG. 19 is a schematic of the combined OCT/PA/IVUS imaging probe.
Figure 20:
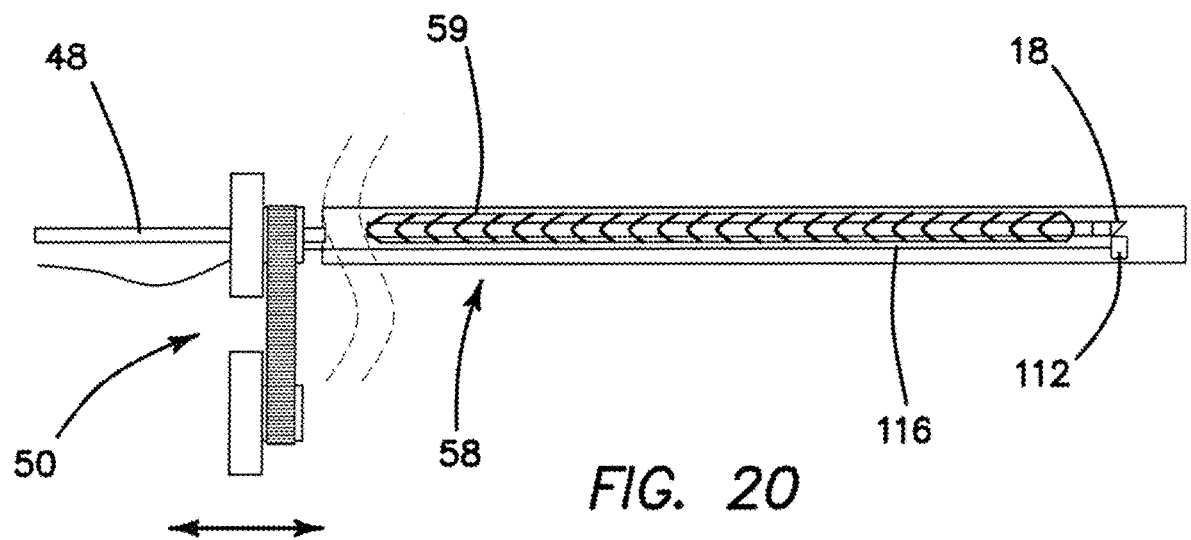
FIG. 20 is a schematic of the combined OCT/PA/IVUS side-by-side imaging probe.
Figure 21C:
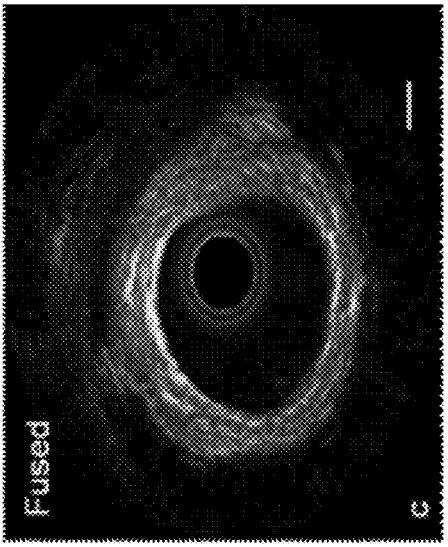
FIG. 21c is an exemplary illustration of photoacoustic-intravascular ultrasound (PA-IVUS) images, specifically a combined IVUS-IVPA image. The scale bars in FIG. 21c represent 1 mm.
Figure 21B:
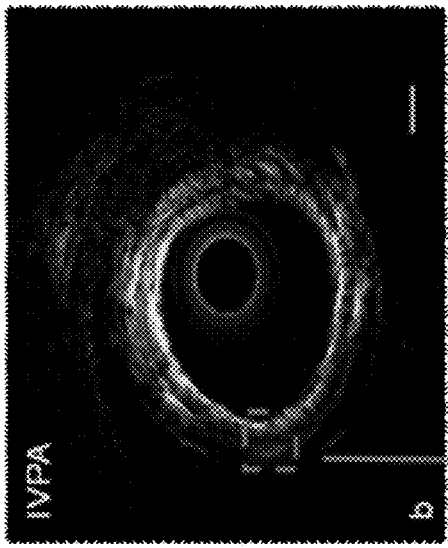
FIG. 21b is an exemplary illustration of photoacoustic-intravascular ultrasound (PA-IVUS) images, specifically a combined IVUS-IVPA image. The scale bars in FIG. 21b represent 1 mm.
Figure 21A:
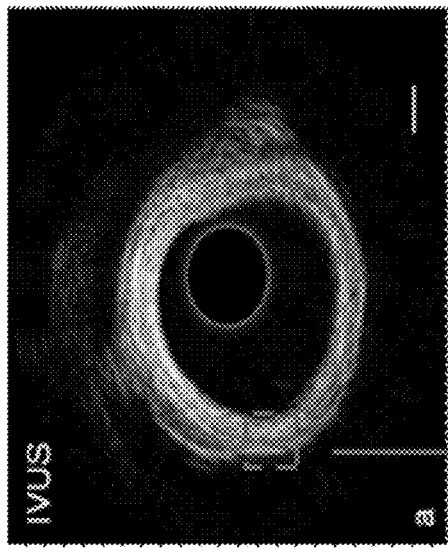
FIG. 21a is an exemplary illustration of photoacoustic-intravascular ultrasound (PA-IVUS) images, specifically an intravascular ultrasound (IVUS) image. The scale bars in FIG. 21a represent 1 mm.
Figure 21F:
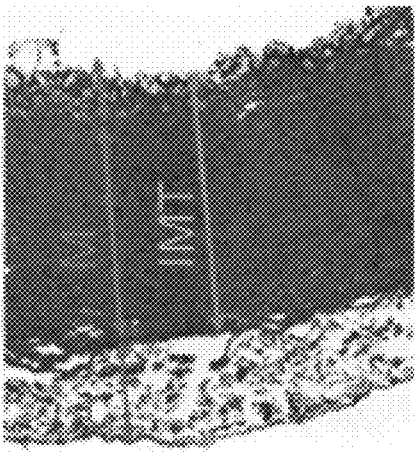
FIG. 21f is a magnified hematoxylin and eosin stain (H&E) histology image of the image seen in FIG. 21c.
Figure 21E:
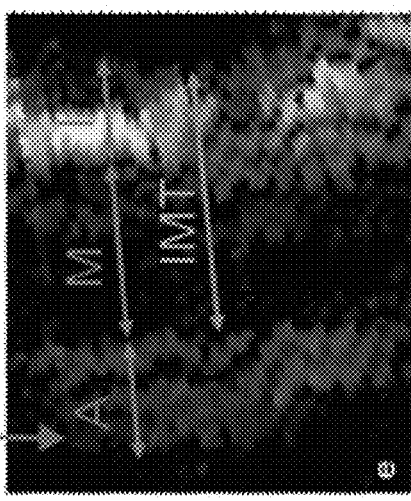
FIG. 21e is a magnified IVPA image of the image seen in FIG. 21b.
Figure 21D:
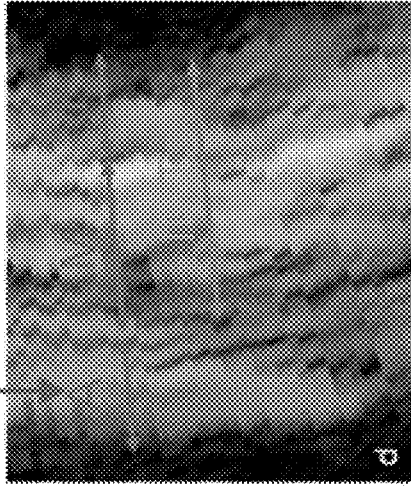
Figure 21G:
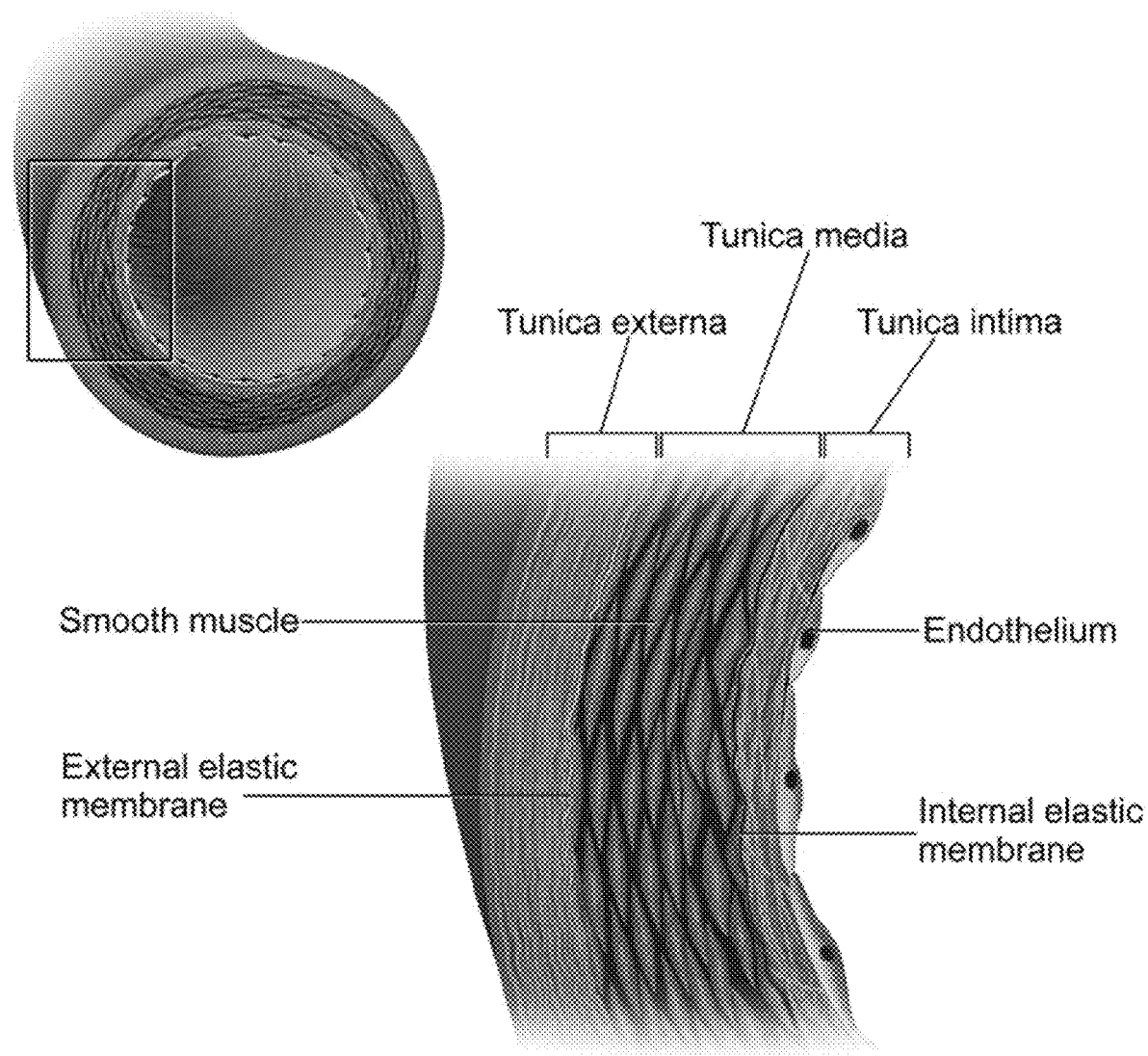
FIG. 21g is an illustration showing the structure of the vessel or artery wall.

One embodiment delivers the OCT and PA signal with a single double cladding fiber (DCF) 48 which goes through the central hollow of the ring-shaped US transducer 122 as shown in FIG. 19. The OCT signal is transported through the core of the DCF 48, and the PA excitation light is delivered through the inner cladding of the DCF 48. Our design steers both the coaxial OCT and PA laser beams together with the US beams into the tissue sample by a 45 degree mirror 124. The US echoes and the excited PA waves from the tissue sample is deflected by the mirror 124 and detected by the US ring transducer 122. A side by side design can also be used for an IVUS-PA-OCT probe as shown in FIG. 20 where the distal end of the OCT probe 18 is longitudinally disposed at approximately the same position as the longitudinal placement of the distal end of ultrasound transducer 112 within catheter 16. FIG. 21a-21f show an exemplary illustrations of PA-IVUS images. It shows the ability to map of optical absorption distribution of tissue constituents and detect the chemical composition of tissue. Tunica intima, I, is the innermost layer of an artery or vein. The middle layer is called the tunica media, M, and the outer layer is called the adventitia, A, or tunica externa as shown in FIG. 21g. The annotations I mark intima and A marks adventitia which have higher absorption coefficients than M marking Media at 532 nm. IVPA has better contrast of I, M, A, and could be used to measure intima-media thickness (IMT). The boxed regions denoted in FIGS. 21 and 21b are shown in the enlarged photographic depictions of FIGS. 21d and 21e respectively.

Doppler OCT:

With the phase-resolved Doppler OCT method (PRDOCT), microvasculature in tissue and the micro-movement down to nanometer range can be imaged and monitored. Traditionally, PROCT uses the phase difference between adjacent A-scans to measure the velocity of the sample movement or moving components in the sample:

$$V \cos(\theta) = \frac{\Delta\phi\lambda_0}{4\pi\Delta T} \quad (1)$$

where ΔT is the time difference between sequential A-line scans, $\lambda_0$ is the central wavelength of the light source and Δϕ is the phase change between sequential A-scans. For an OCT system, minimum detectable Doppler frequency is decided by the minimum resolvable phase difference and the A-line rate of the system The minimum resolvable phase difference is related to the phase stability of the system, and is affected by factors such as mechanical stability of the system and image signal-to-noise ratio (SNR). The phase stability of the system can be determined by statistically analyzing the adjacent A-line phase difference of a static mirror. The minimum resolvable phase difference of typical FD-OCT systems is several milliradians to tens of milliradians. From equation (1), it can be found that the time interval plays an important role in deciding the velocity sensitivity of the D-OCT system. A longer time interval increases the v sensitivity of all the methods. In the cryogenic cooling process monitoring, the PRDOCT algorithm may be performed among the adjacent frames instead of the adjacent A-scans. By applying the algorithm among the adjacent frames, the time interval increases greatly so that the sensitivity increases accordingly. OCT images at the same B-scan location but at different times will be acquired. The PRDOCT algorithm will be used to analyze these images for obtaining the deformation induced by cryogenic cooling. To calculate the phase difference Δϕ in Eqs. (1), the algorithm derived from a cross-correlation algorithm has been shown to offer better performance and is usually preferred. In addition, averaging can be used to improve the signal-noise-ratio. The auto-correlation algorithm together with averaging can be described as:

$$\Delta\phi = \arctan\left\{\frac{\sum_{j=1}^{J}\sum_{z=1}^{N}[\text{Im}(A_{j+1,z})\text{Re}(A_{j,z}) - \text{Im}(A_{j,z})\text{Re}(A_{j+1,z})]}{\sum_{j=1}^{J}\sum_{z=1}^{N}[\text{Re}(A_{j+1,z})\text{Re}(A_{j,z}) - \text{Im}(A_{j,z})\text{Im}(A_{j+1,z})]}\right\} \quad (2)$$

where J is the number of A-lines that are averaged, and N is the number of depth points that are averaged, where $A_{j,z}$ is the complex data at $j_{th}$ A scan and depth of z. The choice of J and N are dependent on the application. The PRDOCT can only monitor the deformation along the incident beam direction. A phase-resolved Doppler variance (PRDV) method can be used to monitor the deformation along the direction perpendicular to the incident beam direction. The PRDV algorithm can be expressed with the help of an auto-correlation algorithm:

$$\sigma^2 = \left[1 - \frac{\left|\sum_{j=1}^{J}\sum_{z=1}^{N}(A_{j+1,z}A_{j,z}^*)\right|}{\frac{1}{z}\sum_{j=1}^{J}\sum_{z=1}^{N}(|A_{j+1,z}|^2 + |A_{j,z}|^2)}\right] \quad (3)$$

PRDOCT and PRDV require high phase-stability of the OCT system. In case of low phase-stability situations, an intensity-based algorithm derived from a modified autocorrelation algorithm can be used to monitor the deformation[24]. In the phase instable situation where there is phase jumping or jittering between adjacent A-lines, the PRDOCT and PRDV values will be affected greatly by the abrupt change in phase terms. The phase instability may produce artifacts, and the performance of the PRDOCT method will be degraded. An intensity based Doppler variance (IBDV) method can minimize the artifact from phase instability. The degree of deformation can be calculated by:

a.

$$\sigma = \left[1 - \frac{\sum_{j=1}^{J}\sum_{z=1}^{N}|A_{j+1,z}A_{j,z}^*|}{\frac{1}{z}\sum_{j=1}^{J}\sum_{z=1}^{N}(|A_{j+1,z}|^2 + |A_{j,z}|^2)}\right] \quad (4)$$

Figure 22:
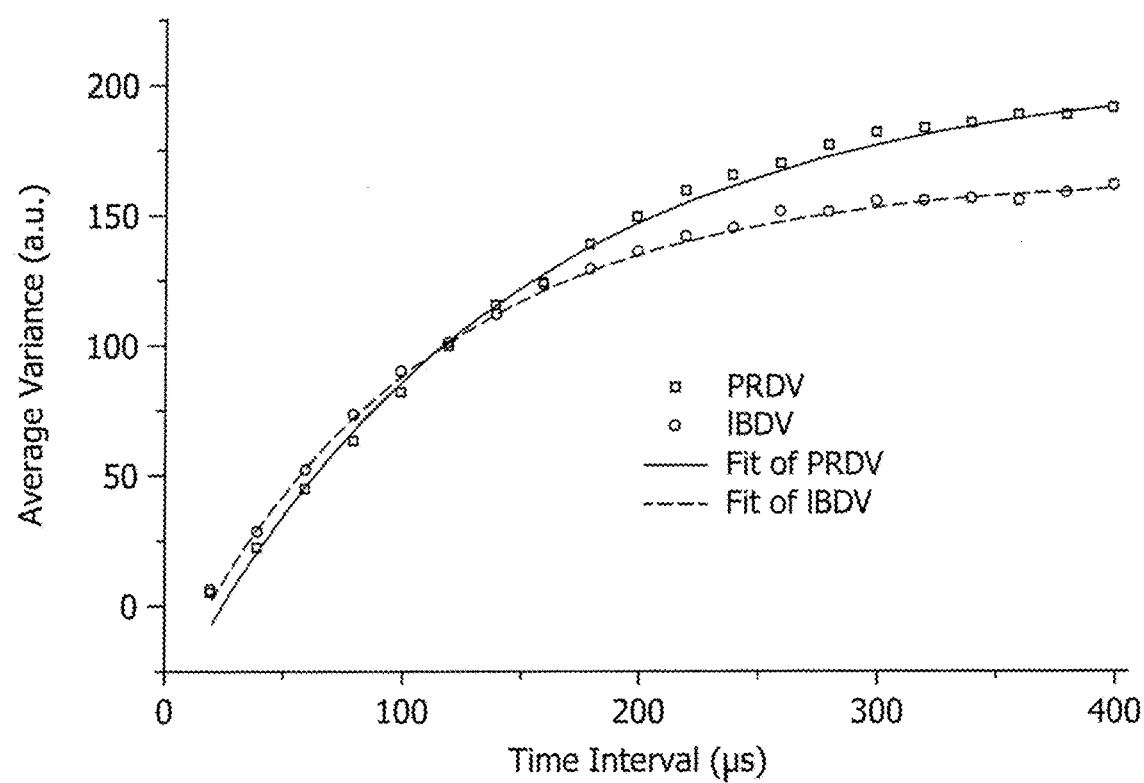
FIG. 22 is a graph of the dependence of IBDV and PRDV values on the time interval.

This sensitivity of the intensity-based algorithm and PRDV can also be increased by increasing the time interval as shown in FIG. 21. FIG. 22 shows the microvasculature of a human volunteer's thigh region imaged by Doppler OCT. Angiogenesis is also a fundamental step in the transition of tumors from a benign state to a malignant one. Angiogenesis plays an essential role of in tumor growth. The Doppler OCT is able to acquire microvasculature down to the capillary level which will prove important and valuable for the diagnosis of cancer.

FIGS. 23a-23g are in-vivo images of human thigh skin. FIG. 23a is a photograph which shows the imaging location within a white rectangle area on the thigh of the volunteer. FIGS. 23b-23e are maximum intensity projections (MIP) of the Doppler OCT images of microcirculation network at different depths of human skin. FIG. 23b is at a depth of 120 μm-360 μm; FIG. 23c at 360 μm-600 μm; FIG. 23d at 600 μm-840 μm; and FIG. 23e at 840 μm-1.3 mm. The arrows indicate new blood vessels detected in each image, and the circles indicate new branches detected in the image. FIG. 23f is an MIP view Doppler OCT image for the depth of 120 μm-360 μm. FIG. 23g is an MIP view Doppler OCT image for the depth of 360 μm-1300 μm. The scale bars in FIG. 23a represent 1 mm.

PS-OCT:

Polarization sensitive optical coherence tomography (PS-OCT) can be used to assess tissue damage by analyzing the change of birefringence in biological tissue, such as collagen, cartilage and muscle. A stable plaque is associated with high collagen content, thicker collagen fibers, and large numbers of smooth muscle cells. In contrast, unstable plaques are likely to have lower collagen content, thinner collagen fibers, and fewer smooth muscle cells. PS-OCT can provide valuable information regarding collagen content, fiber thickness, and SMC density in atherosclerotic plaques. In addition, thermal damage of tissue can be evaluated by the change of birefringence in collagen, a constituent of many biological tissues, whose denaturation takes place at a temperature between 56-65° C.

Figure 24:
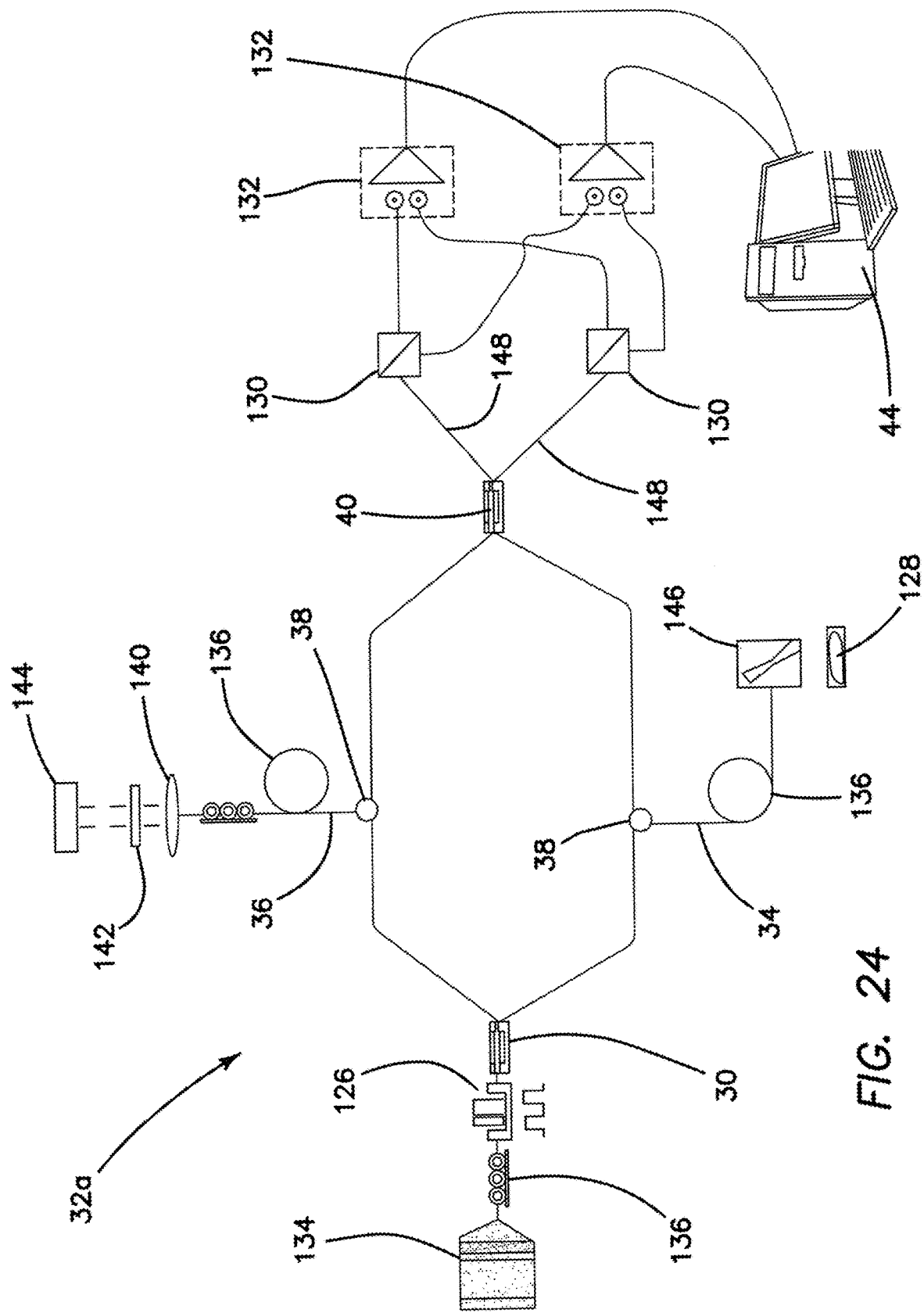
FIG. 24 is a schematic diagram of a PS-OCT system including a static polarization controller SPC; a polarization modulator, PM; a linear polarizer LP; a PM fiber PMF; a polarization beam splitter PBS; and a balanced detector BD.

FIG. 24 depicts a schematic of a fiber-based PSOCT system 32a. System 32a includes a swept source 134 coupled to a static polarization controller 136 (SPC) and then to a polarization modulator 126 (PM). Approximately 20% of the light is coupled by 1×2 coupler 30 to reference arm 36 and 80% of the light is coupled coupler 30 to sample 34 arm 34. Circulator 38 directs the light in the reference arm 36 to static polarization controller 136 (SPC), a collimator 140, a linear polarizer 142 and thence to movable reference mirror 144. Circulator 38 directs the light in the sample arm 34 to static polarization controller 136 (SPC), scanner 146 and thence to sample 128. The measurement signal is then reflected back into scanner 146, static polarization controller 136 (SPC), circulator 38, PM coupler 40 then to PM fibers 148 and balanced detectors 130 (BD). System 32a is modified from the standard OCT system. A polarization modulator 126 is used to control the polarization state of light in the reference arm 36 to ensure that the birefringence measurements will be independent of the orientation of the optical axis of the sample 128. Signals of the slow optical axis and fast optical axis are separated by polarization beam splitters 130 (PBS) and separately collected by two detectors 132 coupled to computer 44. Stokes vectors are commonly used to describe the polarization state of a light beam and can be calculated by signals of the A-scans in computer 44.

Figure 25:
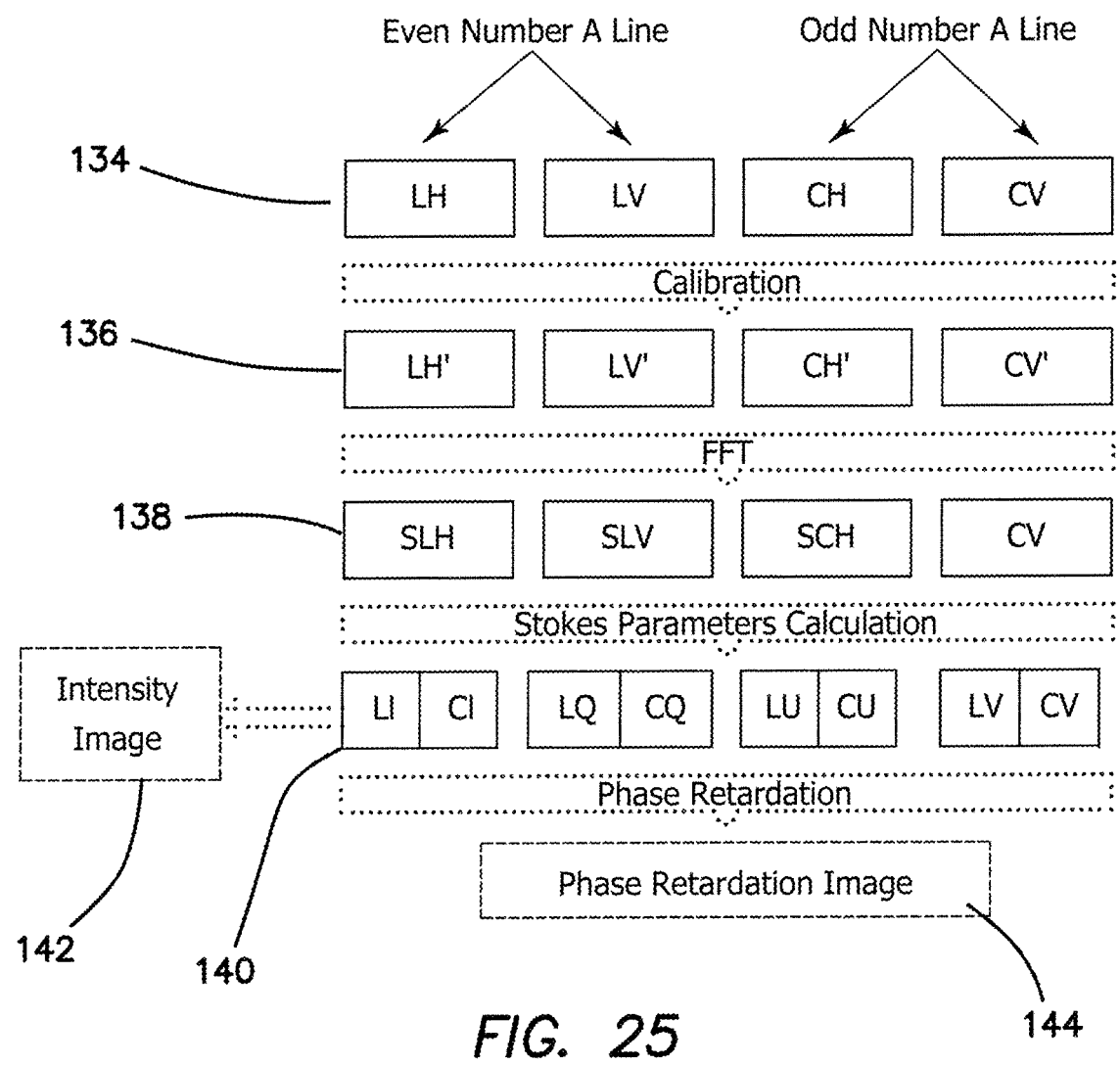
FIG. 25 is a diagram illustrating the flow for processing the PSOCT data. LH (LV) is the acquired horizontally (vertically) polarized component of the interference signal for linear polarization input. CH (CV) is the acquired horizontally (vertically) polarized component of the interference signal for circular polarization input. LH', LV', CH', and CV' are the frequency resampled data for LH, LV, CH, and CV. SLH, SLV, SCH, and SCV are the fast Fourier transforms of LH', LV', CH', and CV'. From SLH and SLV, we can get the Stokes parameters (LI, LQ, LU, and LV) for linear polarization input. Accordingly, we can get the Stokes parameters (CI, CQ, CU, and CV) for circular polarization input. The intensity images were obtained from the average of LI and CI.

The Stokes vector of each lateral pixel can be calculated by four A-lines. The phase retardation of the sample 128 can be calculated from the known polarization states of incident and backscattered light at the sample position, i.e., the rotation of the Stokes vectors in the Poincare sphere. FIG. 25 shows the flow for processing the PSOCT data in computer 44. The data acquired by the two channels of the digitizer of balanced detectors 132 in alternative A-lines are marked as LH, LV, CH, and CV in FIG. 25 in step 134. They represent the detected horizontal (LH) or vertical polarization (LV) signal for linear polarization state input and the detected horizontal (CH) or vertical polarization (CV) signal for circular polarization state inputs. These signals are resampled to linear k space based on a linear interpolation method for calibration at step 136. The resampled signals are marked as LH', LV', CH', and CV'. A fast Fourier Transform FFT is used to convert the resampled data to the complex depth encoded signals (SLH, SLV, SCH, SCV) at step 138. The complex depth encoded signal was used to get the Stokes parameters for linear polarization input (LI, LQ, LU, LV) and circular polarization input (CI, CQ, CU, CV) at step 140. Then the intensity and phase retardation images are obtained at steps 142 and 144 respectively. FIGS. 26a and 26b show a three dimensional reconstructed PSOCT images for pig tendon.

Thermal-OCT System for Tumor Treatment:

For treatment of a tumor, the OCT catheters 16 of the illustrated embodiments are directly placed in the middle of a cryoprobe 146 and a window 148 is opened on the treatment surface 150 of the cryoprobe 146. FIG. 27 illustrates the cryoprobe 146 with the OCT catheter 16 inside. The cryoprobe 146 may be inserted into the tumor or directly placed in contact with the tissue to be or being ablated. The window 148 is opened on the front surface 150 of the cryoprobe 146 to insure the OCT imaging. The OCT imaging unit 12 can help guide the cryoprobe 146 to the exact place before the thermal treatment starts, and the whole treatment process can then be monitored at the same time. The cooling agent flows into the cryoprobe 146 through the inner tube 152 and out of the probe through the outlet 154. The flow and the temperature are both controlled by the pump 15 and the valve 17 as shown in FIGS. 1 and 2.

The cyroprobe 146 can also serve as an RF heating electrode, by connecting an electrode (not shown) to an RF generator (not shown). RF energy is delivered into the tumor tissue resulting in an elevated temperature for tumor cell killing.

In summary, we propose an intravascular diagnosis and therapy system which uses OCT for diagnosis and thermal therapy for the treatment of coronary artery diseases and tumors. OCT offer images of structural details at a higher resolution on the order of 10 microns, which can be used to accurately assess the thickness of a plaque fibrous cap in the case of coronary artery diseases. The OCT images provide valuable guidance information before the thermal angioplasty therapy and the tumor thermal therapy, and also allows monitoring the treatment process to provide useful feedback. The disclosed system may further include IVUS and PA to quantify the full thickness of the plaque, reveal the chemical components of tissue, and monitor the treatment process in deeper tissue regions.

In particular, the illustrated embodiments include a multimodal medical device for the diagnosis and/or treatment of a disease comprising an instrument for performing thermal therapy; and an imaging system having multiple tomographic imaging modes, including optical coherence tomography (OCT), ultrasound imaging, photoacoustic (PA) imaging, fluorescence imaging and/or thermal imaging to provide guidance for accurate diagnosis and treatment of the disease.

The device includes a catheter and probe capable of simultaneous diagnosis and treatment of the disease.

The instrument and imaging system are integrated into a single integrated device.

An integrated diagnosis and therapy catheter system for the accurate diagnosis and treatment of plaques in a vascular system and cancers comprises: an intraoperative imaging catheter to accurately identify a site of lesion and depth of cryosurgery or heating probe placement, and to monitor a process of freezing and/or heating; and an instrument integrated into the intraoperative imaging catheter for performing cryosurgery and/or thermal therapy.

The intraoperative imaging catheter comprises an infrared (IR) thermal camera for temperature monitoring of treatment.

The system further comprises a fiber bundle for delivering an IR signal through the intraoperative imaging catheter.

The intraoperative imaging catheter comprises an intravascular ultrasound imaging (IVUS) system so that cross-sectional images of a vessel wall and of an entire large lipid pool and large tumor region are produced, wherein by the combination of IVUS and OCT the vulnerability, location and size of the large lipid pool and large tumor region are determined.

The intraoperative imaging catheter comprises a photoacoustic (PA) imaging system to provide the mapping of an optical absorption distribution of tissue constituents and detecting the chemical composition of tissue to facilitate identification of a region of plaque and a boundary of a tumor.

The intraoperative imaging catheter comprises a fluorescence cytometry system for diagnosis of cancer.

The intraoperative imaging catheter comprises a fluorescence imaging system to accurately image target molecules in tissue.

The system further comprises a single mode fiber, multimode fiber, dual clad fiber or photonic crystal fiber disposed in the intraoperative imaging catheter for the delivery OCT, PA, or fluorescence excitation light and for the collection of OCT and fluorescence signals.

The intraoperative imaging catheter comprises an imaging system having two or more imaging modalities selected from the group of optical coherent tomography (OCT), intravascular ultra sound (IVUS), photoacoustics (PA) and fluorescence (FL), which are combined and used to accurately identify the location of plaques and tumors with a thermoplasty balloon and/or probe integrated into a single catheter so that operation time is reduced and patient safety is enhanced, where the use of a combination of OCT-IVUS-PA-FL during thermoplasty and/or thermal therapy increases diagnosis accuracy, since the OCT-IVUS-PA-FL is used to monitor the cryoplasty and/or thermal therapy process in real time to improve the treatment effectiveness and accuracy.

The intraoperative imaging catheter includes functional extensions comprising Doppler OCT or polarization sensitive OCT for the imaging of vasculature, collagen, cartilage or nerve.

The intraoperative imaging catheter further includes a Doppler OCT function and polarization sensitive OCT function to provide assessment of a treatment boundary or tissue damage.

The system further includes an OCT imaging probe configured to have a side view design or forward view design and rotated by an external motor or a distal-end micro motor, where a forward view OCT probe includes a lead zirconate titanate material (PZT) or a piezoelectric material or electromagnetic (EM) design, and includes a gradient index (GRIN) lens, GRIN fiber or a ball lens for the purpose of focusing.

The system further includes dual or multiple distill balloons with the intraoperative imaging catheter, where one balloon is used for cryoplasty and/or thermal therapy and the other balloon is used for isolation, so that under the guidance of an image, the location of vascular plaque is accurately diagnosed and located.

The system further includes a subsystem for selectively providing liquid $N_2O$ and another selected freezing agent for different treatment requirements, where a change of freezing agent ensures different freezing treatment capacity.

The system further includes a distill balloon with the intraoperative imaging catheter, where the balloon is used for cryoplasty and/or thermal therapy, the balloon having an let and outlet tube communicating therewith, the inlet tube including a J-T expansion valve for freezing, the J-T expansion valve for transporting a cryoagent into the balloon.

The system further includes a distill balloon with the intraoperative imaging catheter, and one or more RF electrodes on a surface of the balloon to adjust the shape and size of an ablation region, where the one or more RF electrodes are placed inside the balloon.

The system further includes a distill balloon with the intraoperative imaging catheter and a microwave antenna for heating is placed on an exterior or interior surface of the balloon.

The instrument integrated into the intraoperative imaging catheter for performing thermal angioplasty and/or thermal therapy includes a subsystem to generate and deliver infrared light as a heating modality.

The instrument integrated into the intraoperative imaging catheter for performing thermal angioplasty and/or thermal therapy includes an ultrasound transducer as a heating modality.

The instrument integrated into the intraoperative imaging catheter for performing thermal angioplasty and/or thermal therapy includes a laser probe as a heating modality.

The system further includes a distill balloon with the intraoperative imaging catheter and including fluid or gas at a predetermined temperature inside the balloon to protect an endothelial layer of tissue from overheating.

The scope of the illustrated embodiments also extends to a method for intravascular diagnosis and therapy comprising the steps of using OCT imaging for diagnosis and performing thermal therapy for the treatment of coronary artery disease or tumor, where OCT imaging is used before performance of the thermal therapy to identify and determine a position of the coronary artery disease or tumor, and is used during performance to monitor the treatment process and provide feedback regarding the treatment process; and using intravascular ultrasound IVUS or photoacoustics PA to quantify thickness of plaque, reveal the chemical components of tissue, or monitor the treatment process in deeper tissue regions.

Many alterations and modifications may be made by those having ordinary skill in the art without departing from the spirit and scope of the embodiments. Therefore, it must be understood that the illustrated embodiment has been set forth only for the purposes of example and that it should not be taken as limiting the embodiments as defined by the following embodiments and its various embodiments.

Therefore, it must be understood that the illustrated embodiment has been set forth only for the purposes of example and that it should not be taken as limiting the embodiments as defined by the following claims. For example, notwithstanding the fact that the elements of a claim are set forth below in a certain combination, it must be expressly understood that the embodiments includes other combinations of fewer, more or different elements, which are disclosed in above even when not initially claimed in such combinations. A teaching that two elements are combined in a claimed combination is further to be understood as also allowing for a claimed combination in which the two elements are not combined with each other, but may be used alone or combined in other combinations. The excision of any disclosed element of the embodiments is explicitly contemplated as within the scope of the embodiments.

The words used in this specification to describe the various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself.

The definitions of the words or elements of the following claims are, therefore, defined in this specification to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a subcombination or variation of a subcombination.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptionally equivalent, what can be obviously substituted and also what essentially incorporates the essential idea of the embodiments.

We claim:

1. An integrated diagnosis and therapy system for the accurate diagnosis and treatment of a plaque in a vascular system comprising:
    an intraoperative imaging catheter to accurately identify a site of lesion and depth of thermal therapy or probe placement, wherein the imaging catheter is configured to monitor a process of freezing and heating; and
    an instrument integrated into the intraoperative imaging catheter for performing thermal angioplasty and/or thermal therapy,
    wherein the intraoperative imaging catheter comprises a first distal balloon used for cryoplasty of a cooling zone, and a second distal balloon, external to the first distal balloon, used for thermal isolation, so that under the guidance of an image, the location of the vascular plaque is accurately diagnosed and located,
    wherein the first distal balloon comprises one or more RF electrodes on a surface of the first distal balloon to adjust the shape and size of an ablation region for heating of a heating zone,
    wherein the first distal balloon and the second distal balloon are configured to longitudinally divide the interior volume of a lumen when inflated so that the first distal balloon makes contact with the location of the vascular plaque, and the second distal balloon makes contact with the vascular system, the second distal balloon being external to the first distal balloon,
    wherein the first distal balloon is connected to a cryogenic cooling liquid tank and the second distal balloon is connected to a tank comprising a gas or air that is warmer relative to the cryogenic cooling liquid, and
    wherein the instrument is configured to provide simultaneous heating and cooling of the separate heating and cooling zones.

2. The system of claims 1 where the intraoperative imaging catheter comprises an imaging system having two or more imaging modalities selected from the group of optical coherent tomography (OCT), intravascular ultrasound (IVUS), photoacoustics (PA) and fluorescence (FL), which are combined and used to accurately identify the location of vulnerable plaques and tumors with a thermoplasty balloon and/or thermal therapy probe integrated into a single catheter so that operation time is reduced and patient safety is enhanced, where the use of a combination of OCT-IVUS-PA-FL during cryoplasty and/or thermal therapy increases diagnosis accuracy, since the OCTIVUS-PA-FL is used to monitor the cryoplasty and/or thermal therapy process in real time to improve the treatment effectiveness and accuracy.

3. The system of claim 2 further where the intraoperative imaging catheter includes functional extensions comprising Doppler OCT or polarization sensitive OCT for the imaging of vasculature, collagen, cartilage or nerve.

4. The system of claim 2 where the intraoperative imaging catheter further includes a Doppler OCT function and polarization sensitive OCT function to provide assessment of a treatment boundary or tissue damage.

5. A method for intravascular diagnosis and therapy comprising:
    using OCT imaging within an intraoperative imaging catheter for diagnosis and performing thermal therapy for the treatment of coronary artery disease or tumor,
    where OCT imaging is used before performance of the thermal therapy to identify and determine a position of the coronary artery disease or tumor, and is used during performance to monitor the treatment process and provide feedback regarding the treatment process;
    using intravascular ultrasound IVUS or photoacoustics PA within the intraoperative imaging catheter to quantify thickness of plaque, reveal the chemical components of tissue, or monitor the treatment process in deeper tissue regions;
    inflating a first distal balloon disposed on the intraoperative imaging catheter with a cryogenic agent;
    simultaneously performing cryoplasty on a cooling zone of the coronary artery disease or tumor using the inflated first distal balloon; and
    ablating a heating zone of the coronary artery disease or tumor with at least one RF electrode disposed on a surface of the inflated first distal balloon.

* * * * *